(12) United States Patent
Kadowaki et al.

(10) Patent No.: US 7,508,522 B2
(45) Date of Patent: Mar. 24, 2009

(54) REFLECTED LIGHT MEASURING APPARATUS AND REFLECTED LIGHT MEASURING METHOD

(75) Inventors: Yutaka Kadowaki, Sakai (JP); Shu Morikawa, Sakai (JP); Jun Matsumoto, Sakai (JP); Naoki Kimura, Sakai (JP); Shinji Yamamoto, Sakai (JP)

(73) Assignee: Konica Minolta Sensing, Inc., Osaka (JP)

( * ) Notice: Subject to any disclaimer, the term of this patent is extended or adjusted under 35 U.S.C. 154(b) by 400 days.

(21) Appl. No.: 11/047,970

(22) Filed: Jan. 31, 2005

(65) Prior Publication Data

US 2005/0179902 A1  Aug. 18, 2005

(30) Foreign Application Priority Data

Feb. 16, 2004 (JP) .............................. 2004-037829

(51) Int. Cl.
  *G01N 21/55* (2006.01)
(52) U.S. Cl. ....................................... 356/445; 356/446
(58) Field of Classification Search ......... 356/402–407, 356/425, 445–446
  See application file for complete search history.

(56) References Cited

U.S. PATENT DOCUMENTS 5,699,164 A * 12/1997 Lehan et al. ................. 356/445

6,707,553 B1  3/2004 Imura
2004/0066511 A1 * 4/2004 Tanaami et al. ............. 356/318

FOREIGN PATENT DOCUMENTS

| JP | 58-179303    | 10/1983 |
| JP | 2003-215111 A | 7/2000 |
| JP | 2003-156446 A | 5/2003 |
| JP | 2003-215111 A | 7/2003 |
| JP | 2004-020263 A | 1/2004 |

OTHER PUBLICATIONS

Partial translation of Japanese patent publication JP 2003-156446 A published on May 30, 2003, available on homepage of Japanese Patent Office as of 2008, 13 pages.
Partial translation of Japanese patent publication JP 2003-215111 A published on Jul. 30, 2003, available on homepage of Japanese Patent Office as of 2008, 17 pages.
Translation of Office Action for corresponding Japanese patent application 2004-37829.

* cited by examiner

*Primary Examiner*—Gregory J Toatley, Jr.
*Assistant Examiner*—Tri T Ton
(74) *Attorney, Agent, or Firm*—Brinks Hofer Gilson & Lione

(57) ABSTRACT

A reflected light measuring apparatus including an illumination system and a light receiving system which receives reflected light from a measuring area of an object illuminated with measuring light projected from the illumination system. The illumination system projects the measuring light with a prescribed angular width onto each point in the measuring area. The illumination system and the light receiving system project the measuring light onto the measuring area and receive the reflected light via a telecentric optical system.

6 Claims, 16 Drawing Sheets

REFLECTED LIGHT MEASURING APPARATUS AND REFLECTED LIGHT MEASURING METHOD

This application is based on application No. 2004-37829 filed in Japan, the content of which is hereby incorporated by reference.

BACKGROUND OF THE INVENTION

1. Field of the Invention

The present invention relates to a reflected light measuring apparatus and a reflected light measuring method which project measuring light onto an object to be measured and receive its reflected light for various sensing purposes.

2. Description of the Related Art

Various kinds of reflected light measuring apparatuses are known in the prior art which project measuring light onto an object to be measured and receive and analyze its reflected light for such purposes as color evaluation, surface condition detection, and other sensing operations.

FIG. 13 is a schematic diagram showing the basic configuration of such a reflected light measuring apparatus. The apparatus shown is constructed such that the measuring light emitted from a spot light source (spot-like light source) 10 such as a halogen lamp, xenon lamp, or LED is projected onto a specimen 20 to be measured, and its reflected light is directed through a light receiving lens 30 to a light receiving sensor 40 such as a photodiode or CCD. Here, rays of light emitted from the spot light source 10 are first passed through a beam regulating plate 101 for conversion into parallel rays of light which are projected onto the surface of the specimen 20 to be measured.

FIG. 14 is a schematic diagram showing in simplified form the configuration of a reflected light measuring apparatus employing a multidirectional illumination, unidirectional light receiving method which is used, for example, in a multi-angle calorimeter or the like. The basic configuration of this reflected light measuring apparatus is the same as that shown in FIG. 13, the only difference being that the measuring light is projected onto the specimen 20 from a plurality of angles.

The example shown in FIG. 14 uses two light illumination systems: a highlight illumination system 50 whose angle (indicated by θ1 in the figure) to the normal to the surface of the specimen 20 is relatively small, and a shade illumination system 60 whose angle (indicated by θ2 in the figure) to the normal to the specimen surface is relatively large. The highlight illumination system 50 and the shade illumination system 60 comprise spot light sources 500 and 600, beam regulating plates 501 and 601, and lenses 502 and 602, respectively, and are constructed so that parallel rays of light as the measuring light from the respective light sources can be projected onto the surface of the specimen 20 at angles θ1 and θ2, respectively.

Reflected light measuring apparatuses employing such a multidirectional illumination, unidirectional light receiving method are used for such purposes as sensing the surfaces of specimens whose reflected light intensities vary depending on the viewing angle, for example, in calorimeters that measure metallic paint or pearly paint colors used for automobiles, etc.

When the measuring light emitted from the spot light source 10 is projected as parallel rays of light onto the specimen 20 to be measured, as in the prior art shown in FIG. 13, the resulting reflection characteristics are as shown in FIG. 15 when the measuring area surface of the specimen 20 is a horizontal plane surface. That is, in FIG. 15, Q10, Q20, and Q30 show the reflection characteristics (for example, the light intensity distribution of light of specific wavelength) obtained when the measuring light rays P1, P2, and P3 as parallel rays of light are projected onto and reflected from arbitrarily taken points A, B, and C, respectively, on the measurement surface (horizontal measuring area surface) 20S of the specimen 20.

In the figure, h10, h20, and h30 indicate the specular reflections of the measuring light rays P1, P2, and P3 (that is, the reflected light rays are symmetric to the incident rays with respect to the normal to the measurement surface 20S). In this case, since the measurement surface 20S of the specimen 20 is a horizontal plane surface, the reflection characteristics Q10, Q20, and Q30 are the same (that is, the reflection characteristics are the same within the measuring area surface), and stable measurements can thus be accomplished without causing any particular measurement errors within the measuring area surface.

However, when the measuring area surface of the specimen 20 is a curved surface, if the measuring light is projected in the form of parallel rays of light, the angles of the reflected light rays (the angles of the specularly reflected light rays) differ from each other within the measuring area surface, and this causes measurement errors.

FIG. 16 shows the reflection characteristics when the measuring area surface 20S of the specimen 20 is a curved surface of radius "r". As shown, when the measuring light rays P1, P2, and P3 as parallel rays of light are projected onto the arbitrarily taken points A, B, and C on the measurement surface 20S, the specularly reflected light rays from the respective points are h11, h21, and h31 shown by solid lines in the figure, exhibiting the reflection characteristics Q11, Q21, and Q31 based on the specularly reflected light rays h11, h21, and h31, respectively.

Here, when the point B is considered as the reference point of the normal, since the measurement surface 20S is a curved surface, the reflection characteristics Q11 and Q31 at the points A and C are displaced from the reflection characteristics Q10 and Q30 (indicated by dotted lines in the figure) obtained when the measurement surface 20S is a horizontal plane surface, and these displacements show up as measurement errors.

Generally, a reflection characteristic is a combination of the characteristic due to diffused reflection that has no angle dependence and the characteristic due to specular reflection. In each of the above reflection characteristics Q10 to Q31, the gently sloping portion is the characteristic due to diffused reflection, and the sharply pointed portion in the center is the characteristic due to specular reflection. It therefore follows that as the direction in which the reflected light to be sensed is received becomes closer to the direction of the specular reflection, a greater difference is caused in the reflection characteristic even by a slight change in angle. This will be explained with reference to FIG. 17.

Suppose that the measuring light rays P1, P2, and P3 as parallel rays of light are projected as shown in the figure onto the arbitrarily taken points A, B, and C on the measurement surface 20S, and that the measuring reflected light rays to be received for sensing the reflection characteristics at the respective points are defined as shown by h1s, h2s, and h3s in the figure. Here, the specular reflections at the points A, B, and C, due to the incidence of the measuring light rays P1, P2, and P3, are as shown by h11, h21, and h31, respectively, the directions of which are relatively close to those of the measuring reflected light rays h1s, h2s, and h3s.

In this case, the reflection characteristic Q11 at the point A exhibits a characteristic more or less straightened up toward the plumb line compared with the reflection characteristic Q10 obtained when the measurement surface 20S is a horizontal plane surface, while on the other hand, the reflection characteristic Q31 at the point C exhibits a characteristic more or less tilted toward the horizontal line compared with the horizontal plane reflection characteristic Q30.

Here, because the directions of the specular reflections h11, h21, and h31 are close to those of the measuring reflected light rays h1s, h2s, and h3s, the measuring reflected light ray h1s at the point A exhibits a large reflection characteristic value (the value at the intersection d1 where h1s intersects a sloping side of the sharply pointed portion of the reflection characteristic Q11), whereas the measuring reflected light ray h3s at the point C exhibits a small reflection characteristic value (the value at the intersection d2 where h3s intersects the rising section of the sharply pointed portion of the reflection characteristic Q31).

As a result, although the angle difference between the points A and C is very small, a large difference equivalent to the difference Δd between the reflection characteristic values at the intersections d1 and d2 occurs between the reflection characteristics, resulting in the problem that the measurement error within the measuring area surface appreciably increases.

Another problem is that, in the reflection light measuring apparatus shown in FIG. 14, it is difficult to project the parallel rays of light over the entire measuring area surface with the highlight illumination system 50 whose angle θ1 to the normal to the surface of the specimen 20 is relatively small.

That is, when the angle θ1 to the normal to the specimen surface is relatively small, the amount of illumination (the illumination area) necessary to illuminate the entire measuring area surface increases, making it difficult to illuminate the entire measuring area with the parallel rays of light. By contrast, with the shade illumination system 60 whose angle θ2 to the normal to the specimen surface is relatively large, since the measuring light is incident at a large angle on the measuring area surface, the entire measuring area surface can be illuminated with a relatively small amount of illumination, and it is therefore easy to ensure the parallelism of the light rays; with the highlight illumination system 50, on the other hand, it is not easy to ensure the parallelism of the light rays, the resulting problem being that a large-size optical system becomes necessary if the parallelism is to be ensured.

The reflection characteristic diagrams of FIGS. 15 to 17 assume that the measuring light rays P1, P2, and P3 incident on the measurement surface 20S are parallel rays of light, but if the parallelism is not ensured, variations will occur in the angle of specular reflection, which can incur another error.

SUMMARY OF THE INVENTION

It is accordingly an object of the present invention to provide a reflected light measuring apparatus and a reflected light measuring method that can suppress measurement errors as far as possible, even when the measuring area surface of the specimen is a curved surface which inevitably causes differences in the reflection characteristics within the measuring area surface.

It is another object of the present invention to provide a reflected light measuring apparatus and a reflected light measuring method that can accomplish stable measurements without increasing the size of the measuring apparatus, even when the measuring light is projected from a direction whose angle to the normal to the specimen surface is relatively small.

To achieve the above objects, according to one aspect of the present invention, there is provided a reflected light measuring apparatus comprising an illumination system which projects measuring light onto a measuring area of an object to be measured, and a light receiving system which receives reflected light from the measuring area illuminated with the measuring light projected from the illumination system, wherein the illumination system is configured to be able to project the measuring light with a prescribed angular width onto each point in the measuring area of the object to be measured, and the illumination system and the light receiving system are configured to project the measuring light onto the measuring area and receive the reflected light from the measuring area, respectively, via a telecentric optical system.

According to the above reflected light measuring apparatus, since the measuring light from the illumination system is projected with a prescribed angular width onto each point in the measuring area of the object to be measured, the resulting reflection characteristic is such that the sharpness of the characteristic near its specular reflection is reduced, thus suppressing an error associated with an angular change; as a result, even when the measuring surface area is a curved surface, the reflected light can be measured without incurring an appreciable error.

Further, since the measuring light is projected onto the measuring area via the telecentric optical system and the reflected light is received from the measuring area again via the telecentric optical system, the projection angle of the measuring light to be projected and the receiving angle of the reflected light to be received can be made uniform; this also serves to suppress the measurement error. Therefore, even in a measuring environment in which the measuring area surface is a curved surface which inevitably causes differences in reflection characteristics, the occurrence of errors can be suppressed as far as possible, and this can be accomplished without incurring an increase in apparatus size.

According to another aspect of the present invention, there is provided a reflected light measuring apparatus comprising an illumination system which projects measuring light onto a measuring area of an object to be measured, and a light receiving system which receives reflected light from the measuring area illuminated with the measuring light projected from the illumination system, wherein the illumination system includes a highlight illumination system which projects the measuring light from a direction whose angle to a normal to the measuring area of the object to be measured is relatively small and a shade illumination system which projects the measuring light from a direction whose angle to the normal to the measuring area of the object to be measured is relatively large, and wherein the highlight illumination system is configured to be able to project the measuring light with a prescribed angular width onto each point in the measuring area of the object to be measured, and the highlight illumination system and the light receiving system are configured to project the measuring light onto the measuring area and receive the reflected light from the measuring area, respectively, via a telecentric optical system.

That is, in the reflected light measuring apparatus employing a multidirectional illumination, unidirectional light receiving method, the highlight illumination system which projects the measuring light from the direction whose angle to the normal to the measuring area of the object to be measured is relatively small is configured to project the measuring light with a prescribed angular width onto each point in the measuring area of the object to be measured, and provisions are made to project the measuring light onto the measuring area and receive the reflected light from the measuring area via the telecentric optical system. Therefore, even in a measuring environment in which the measuring area surface is a curved surface which inevitably causes differences in reflection characteristics, the occurrence of errors can be suppressed as far as possible, and this can be accomplished without incurring an increase in apparatus size.

According to still another aspect of the present invention, there is provided a reflected light measuring method which projects measuring light onto a specimen having a curved surface and measures a reflection characteristic by receiving the resulting reflected light, wherein the measuring light is projected with a prescribed angular width onto each point on the curved surface of the specimen, and the measurement is performed by making the projection angle of the measuring light to the curved specimen and the receiving angle of the reflected light from the curved specimen respectively the same within the curved surface of the specimen through the use of a telecentric optical system.

With the above reflected light measuring method also, similar effects to those achieved with the above reflected light measuring apparatus can be obtained.

These and other objects, advantages and features of the invention will become apparent from the following description thereof taken in conjunction with the accompanying drawings, which illustrate specific embodiments of the invention.

BRIEF DESCRIPTION OF THE DRAWINGS

In the following description, like parts are designated by like reference numbers throughout the several drawings.

DETAILED DESCRIPTION OF THE PREFERRED EMBODIMENTS

Before proceeding to the detailed description of the embodiments, the principle explanations will be made. That is, the following two points will be explained.

(1) The illumination system is configured to be able to project light with a prescribed angular width onto each point on the measuring area surface of the object to be measured.

(2) The illumination system projects measuring light onto the measuring area via a telecentric optical system, and the light receiving system receives reflected light from the measuring area likewise via the telecentric optical system.

Figure 1A:
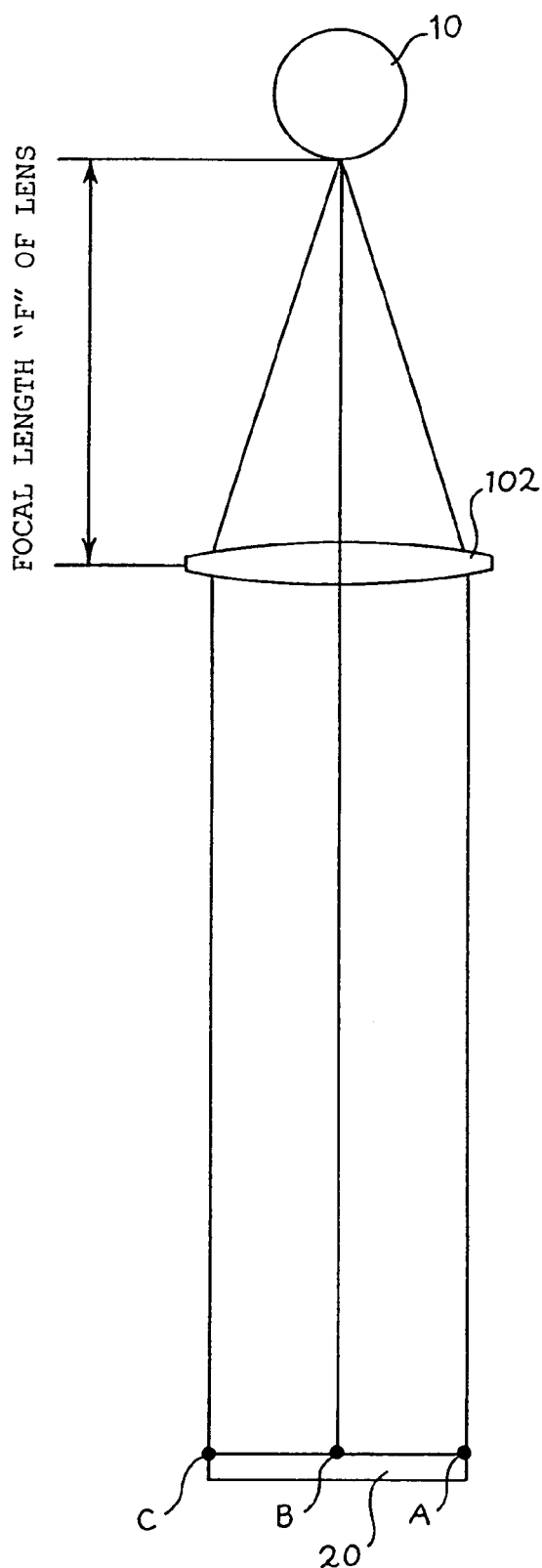
FIGS. 1A and 1B are explanatory diagrams for explaining how the projection of the measuring light to a specimen under measurement differs between different types of illumination system.

First, point (1) will be explained with reference to FIGS. 1A to 3. As earlier described, when a spot light source 10 is used as the illumination system as shown in FIG. 1A, the light emitted as the measuring light from the spot light source 10 is converted into parallel rays of light by an optical lens 102 placed away from the light source by a distance equal to its focal length F, and the measuring light thus made parallel is projected onto the specimen 20 to be measured. When the measuring light is projected in this manner, if the surface of the specimen 20 is a curved surface, for example, the measuring error will increase as previously described.

Figure 1B:
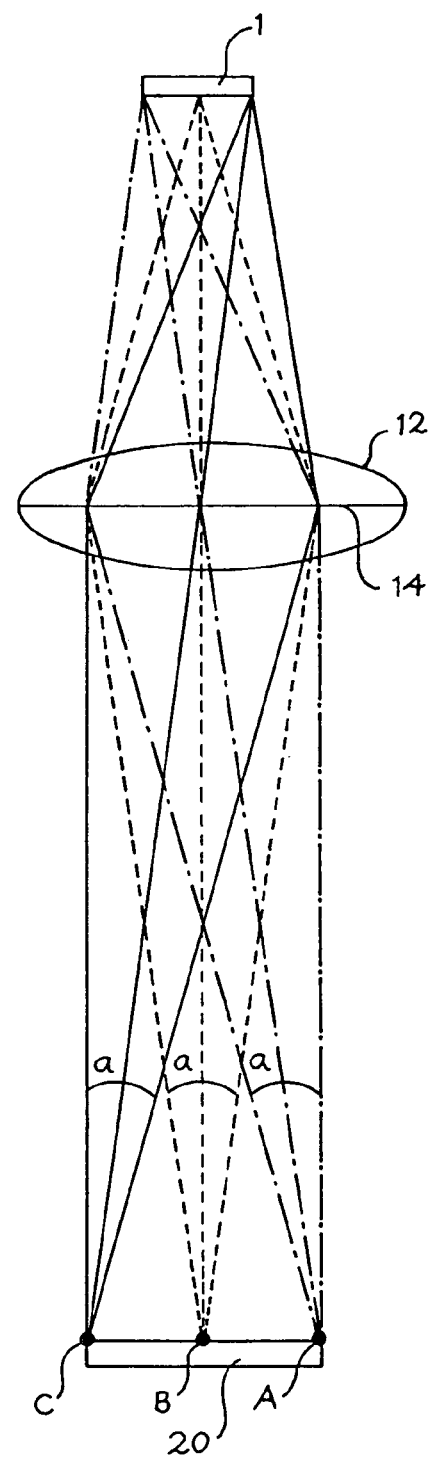

By contrast, when an area light source 1 such as shown in FIG. 1B is used as the illumination system with provisions made to project an image of the area light source onto the surface of the specimen 20 through a condenser lens 12 (light schematically shown to be focused along centerline 14 of condenser lens 12) placed in front of the light source, that is, to project the measuring light with a prescribed angular width "a" onto each of the points A, B, and C on the measuring area surface of the specimen 20, then the following effect occurs.

Figure 2:
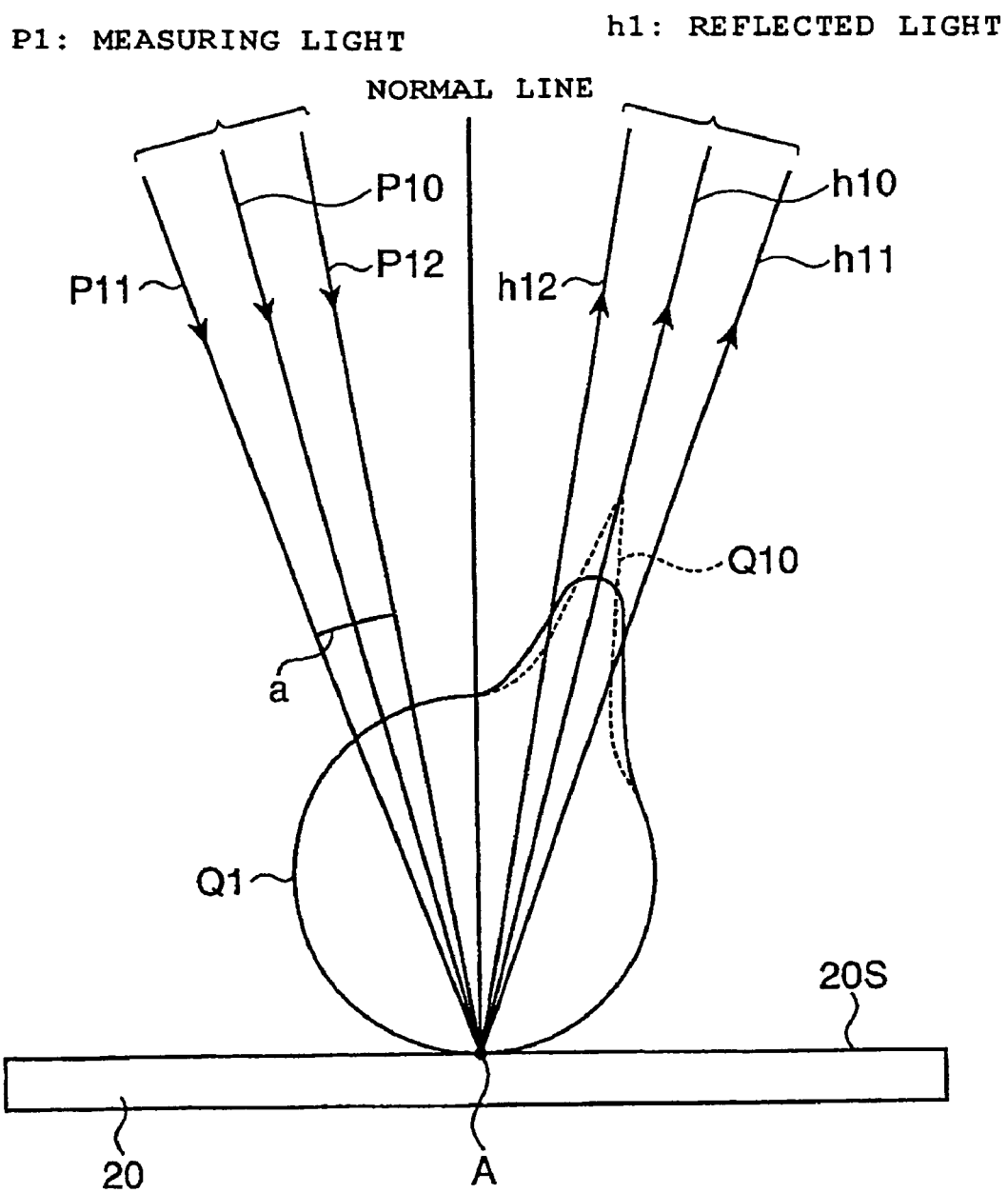
FIG. 2 is a reflection characteristic diagram showing a reflection characteristic Q1 when the measuring light having a prescribed angular width is projected onto a point A on a measurement surface.
Figure 15:
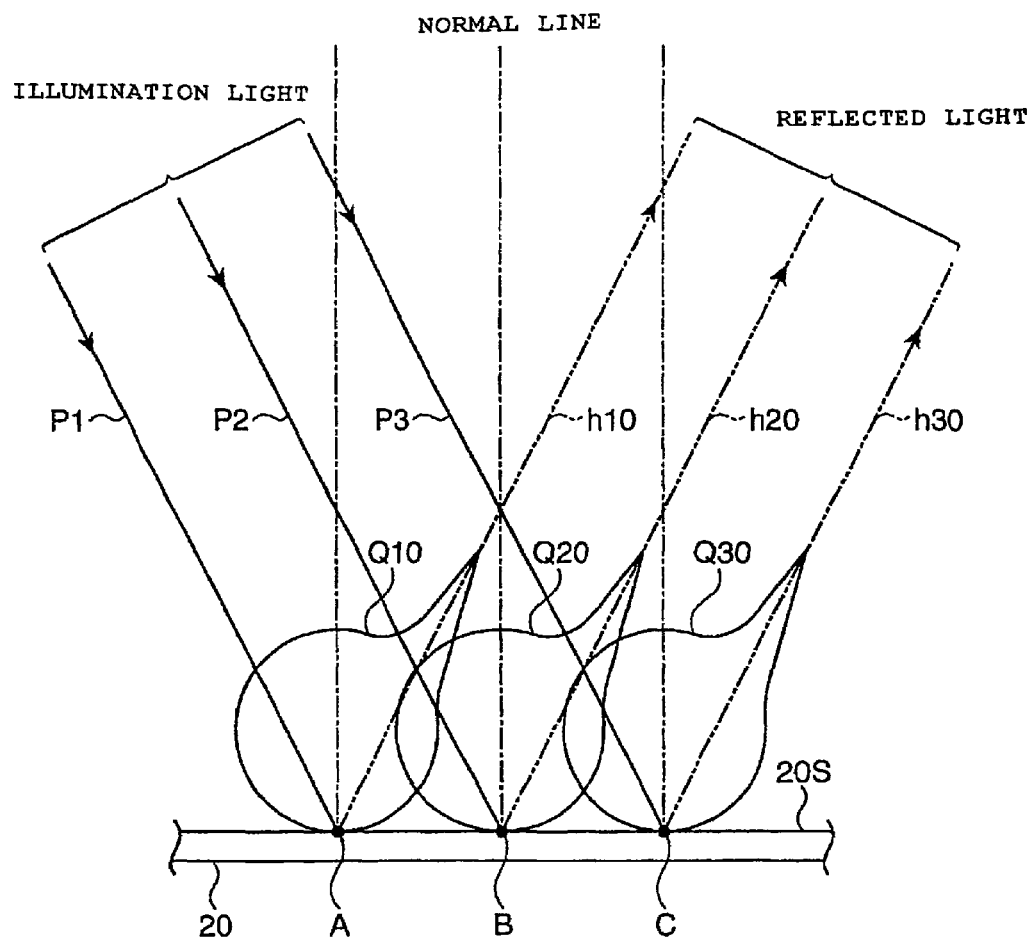
FIG. 15 is a characteristic diagram showing reflection characteristics measured on a specimen by the reflected light measuring apparatus of the prior art.

FIG. 2 is a diagram showing a reflection characteristic Q1 when the measuring light P1 having the prescribed angular width "a" is projected onto the point A on the measurement surface 20S of the specimen 20. As previously described with reference to FIG. 15, when the measuring light is projected in the form of parallel light (for example, only P10 in FIG. 2 is projected), the resulting reflection characteristic Q10 exhibits a sharply pointed shape centered about its specularly reflected light h10.

By contrast, in the case of the measuring light P1 having the prescribed angular width "a", since its specularly reflected light is spread out, that is, since specularly reflected light rays h10, h11, and h12 occur due to the incidence of the measuring light rays P10, P11, and P12, the resulting reflection characteristic Q1 has a pear-like shape with a rounded point. This serves to reduce variations in reflection characteristic caused by variations in angle, and as a result, even when an angular shift occurs in the reflected light to be received, the effect on the measured value is correspondingly reduced.

Figure 3:
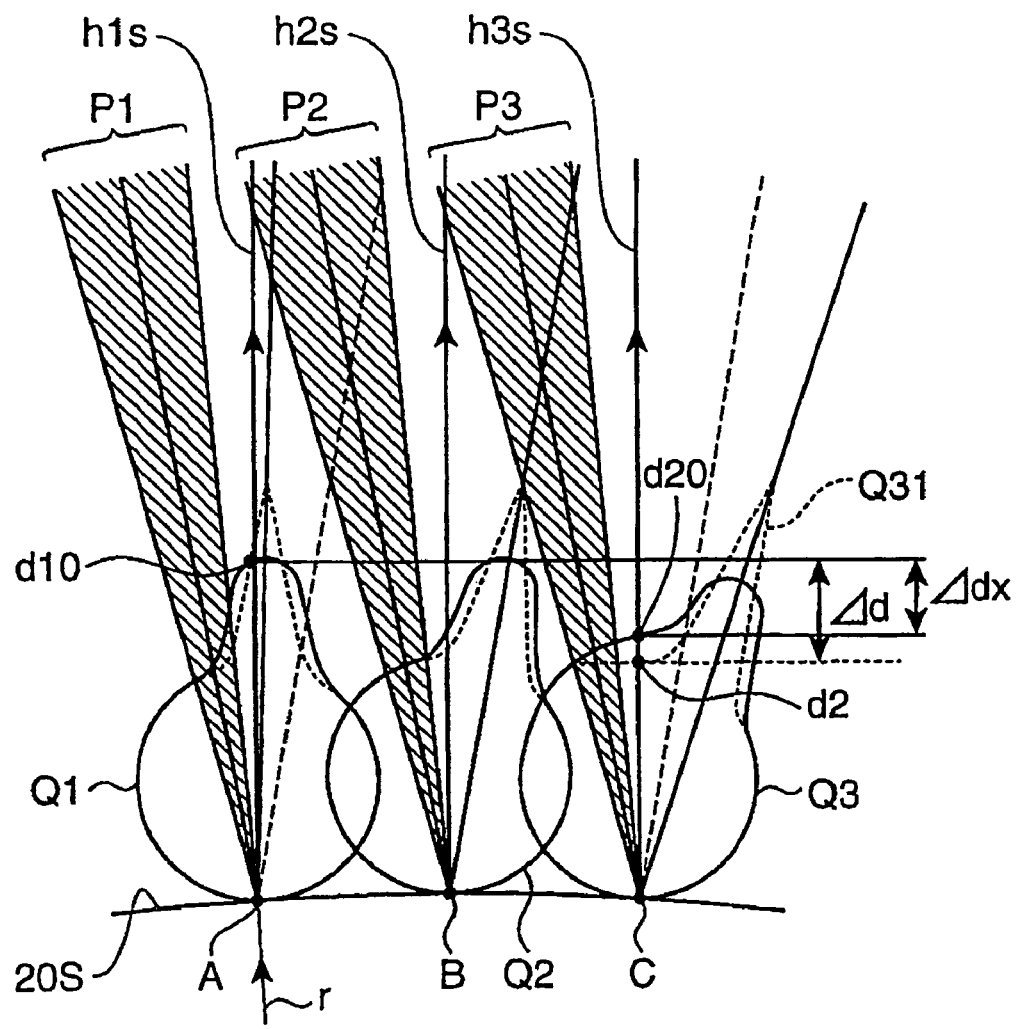
FIG. 3 is a reflection characteristic diagram for explaining how a measurement error occurs when the measurement surface is a curved surface.
Figure 17:
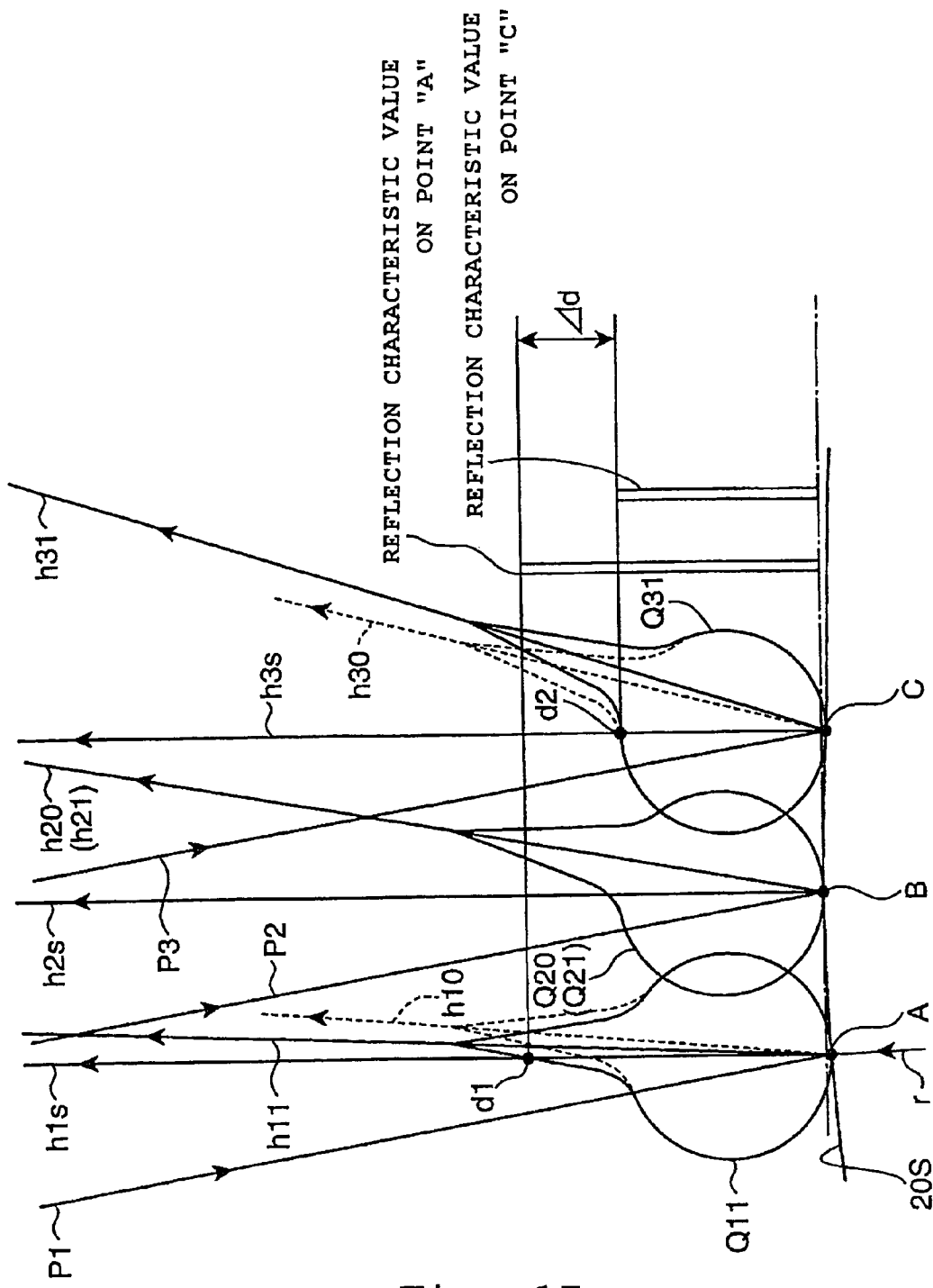
FIG. 17 is a characteristic diagram for explaining a factor causing an error when the measuring surface of the specimen under measurement is a curved surface.

That is, when the measurement surface 20S of the specimen 20 is a curved surface of radius r, the measurement error within the measuring area surface can be reduced, as shown in FIG. 3. FIG. 3 is a reflection characteristic diagram corresponding to FIG. 17; as shown, the measuring light rays P1, P2, and P3 each having the prescribed angular width are projected onto the arbitrarily taken points A, B, and C on the measurement surface 20S, and the measuring reflected light rays to be received for sensing the reflection characteristics at the respective points are defined as indicated by h1s, h2s, and h3s in the figure.

In this case, the reflection characteristics Q1, Q2, and Q3 at the points A, B, and C are each characterized in that the sharp point near the specularly reflected light is rounded as described above. Further, since the measurement surface 20S is a curved surface, when viewed relative to the point B the reflection characteristic Q1 at the point A exhibits a characteristic more or less straightened up toward the plumb line compared with the reflection characteristic obtained when the measurement surface 20S is a horizontal plane surface, while on the other hand, the reflection characteristic Q3 at the point C exhibits a characteristic more or less tilted toward the horizontal line compared with the horizontal plane reflection characteristic.

Here, the measurement error between the point A and the point C is defined by the difference Δdx between the reflection characteristic value of the measuring reflected light ray h1s (the value at the intersection d10 where h1s intersects the reflection characteristic Q1) and the reflection characteristic value of the measuring reflected light ray h3s (the value at the intersection d20 where h3s intersects the reflection characteristic Q3), and this difference is smaller than the reflection characteristic value difference Δd occurring when the measuring light is a beam of parallel rays.

More specifically, when the reflection characteristic at point C is noted, the reflection characteristic value of the measuring reflected light ray h3s at the point C is larger in the reflection characteristic Q3 (the value at the intersection d20) when the measuring light having the prescribed angle is projected, compared with the corresponding value in the reflection characteristic Q31 (the value at the intersection d2) when the measuring light of parallel rays is projected; this is because the sharp point near the specularly reflected light is rounded in the former case. As a result, even when the measurement surface 20S is a curved surface, the measurement error within the measuring area surface can be reduced.

Figure 4:
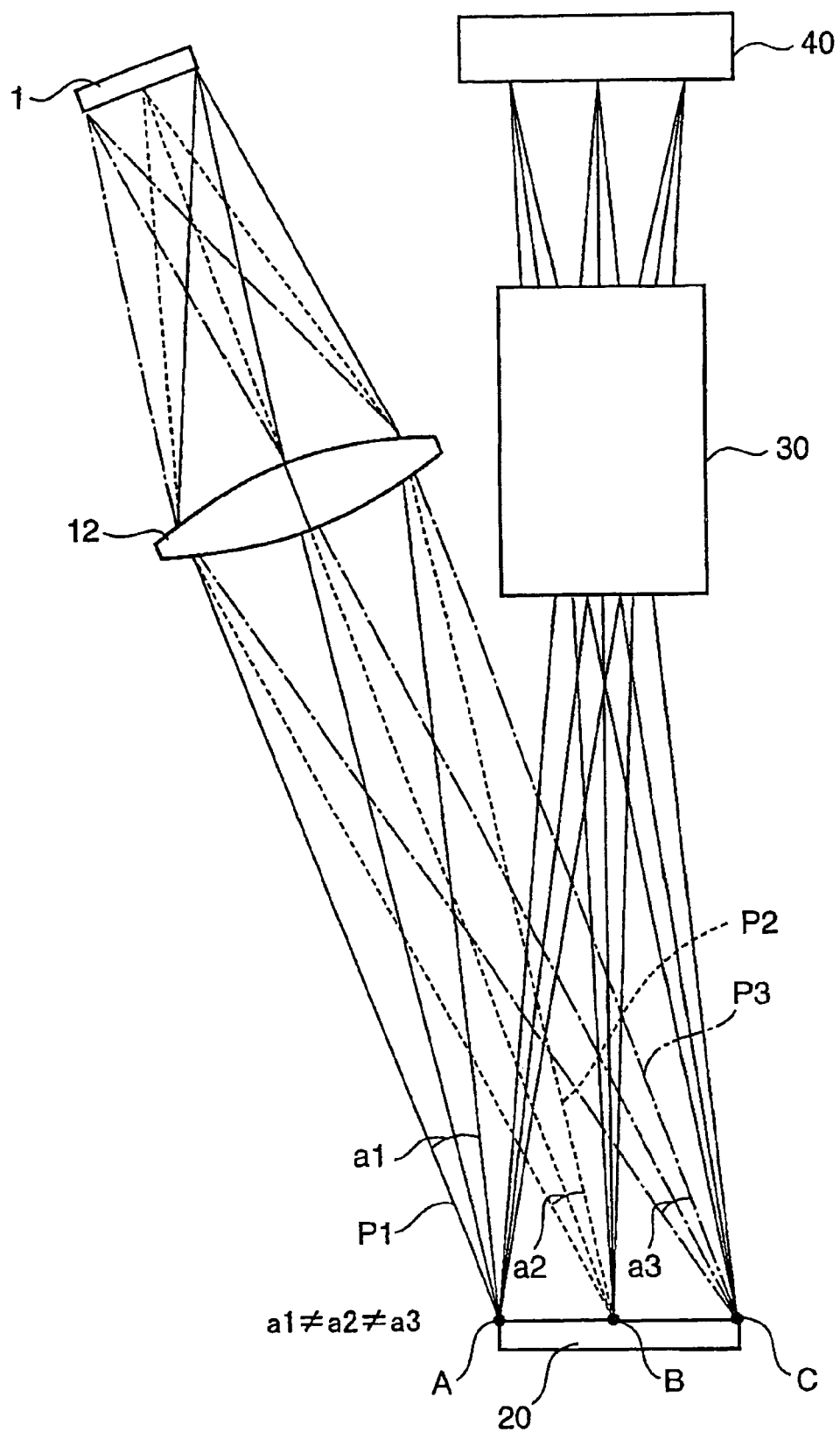
FIG. 4 is a schematic diagram for explaining how the measuring light is projected by an illumination system.
Figure 5:
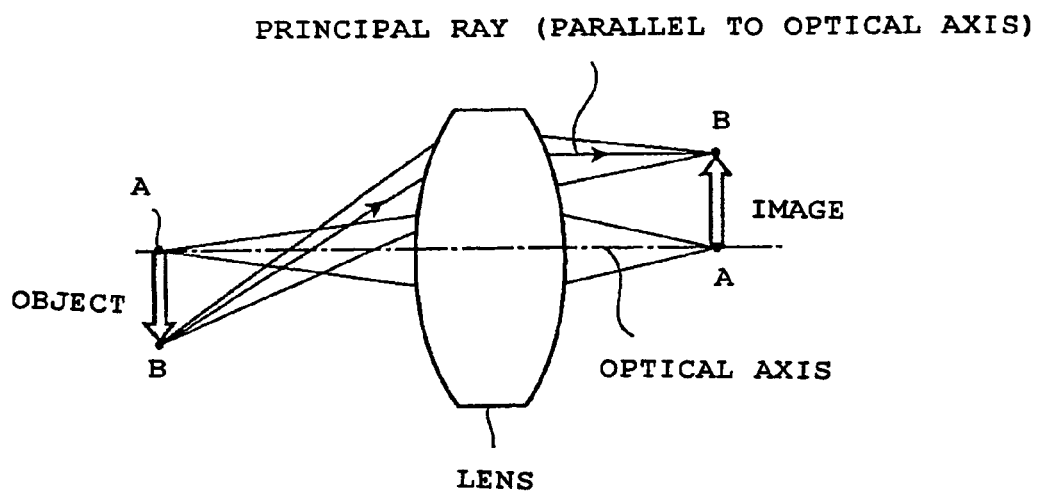
FIG. 5 is a schematic diagram showing the configuration of a telecentric optical system.

Next, point (2) will be explained with reference to FIGS. 4 to 6. FIG. 4 is a diagram showing the configuration of a reflected light measuring apparatus which uses the illumination system shown in FIG. 1B. As previously described, when projecting the measuring light from a direction whose angle to the normal to the surface of the specimen 20 is relatively small, the amount of illumination (the illumination area) necessary to illuminate the entire measuring area surface increases, and it is therefore difficult to illuminate the entire measuring area with the parallel rays of light unless the size of the illumination system is made considerably large.

Accordingly, in the case of a small-size illumination system, the measuring light rays P1, P2, and P3 emitted from the area light source 1, and projected through the condenser lens 12 onto the respective points A, B, and C on the specimen 20, have respectively different angular widths a1, a2, and a3. That is, the measuring light rays are projected at different angles onto the measuring area surface of the specimen 20, which can incur another error.

Further, a similar phenomenon occurs when receiving the reflected light rays. That is, when the reflected light rays from the measuring area surface of the specimen 20 are focused through a receiving lens 30 onto a light receiving sensor 40 which is an area sensor such as a CCD, the incidence angles of the reflected light rays incident on the light receiving sensor 40 cannot be made the same for all the rays reflected from the measuring area surface of the specimen 20, unless the size of the optical system is made considerably large as in the above case.

These problems can be solved by projecting the measuring light onto the measuring area surface of the specimen 20 via a telecentric optical system and receiving the reflected light from the measuring area surface again via the telecentric optical system. FIG. 5 shows an image-side telecentric optical system; this optical system has the property that the principal rays on the image side do not intersect the optical axis however far they is extended (the principal rays are parallel to the optical axis). That is, the principal ray from point B on the object side can be made parallel to the optical axis (the principal ray from point A in FIG. 5) when focused on the image side through the lens.

Figure 6:
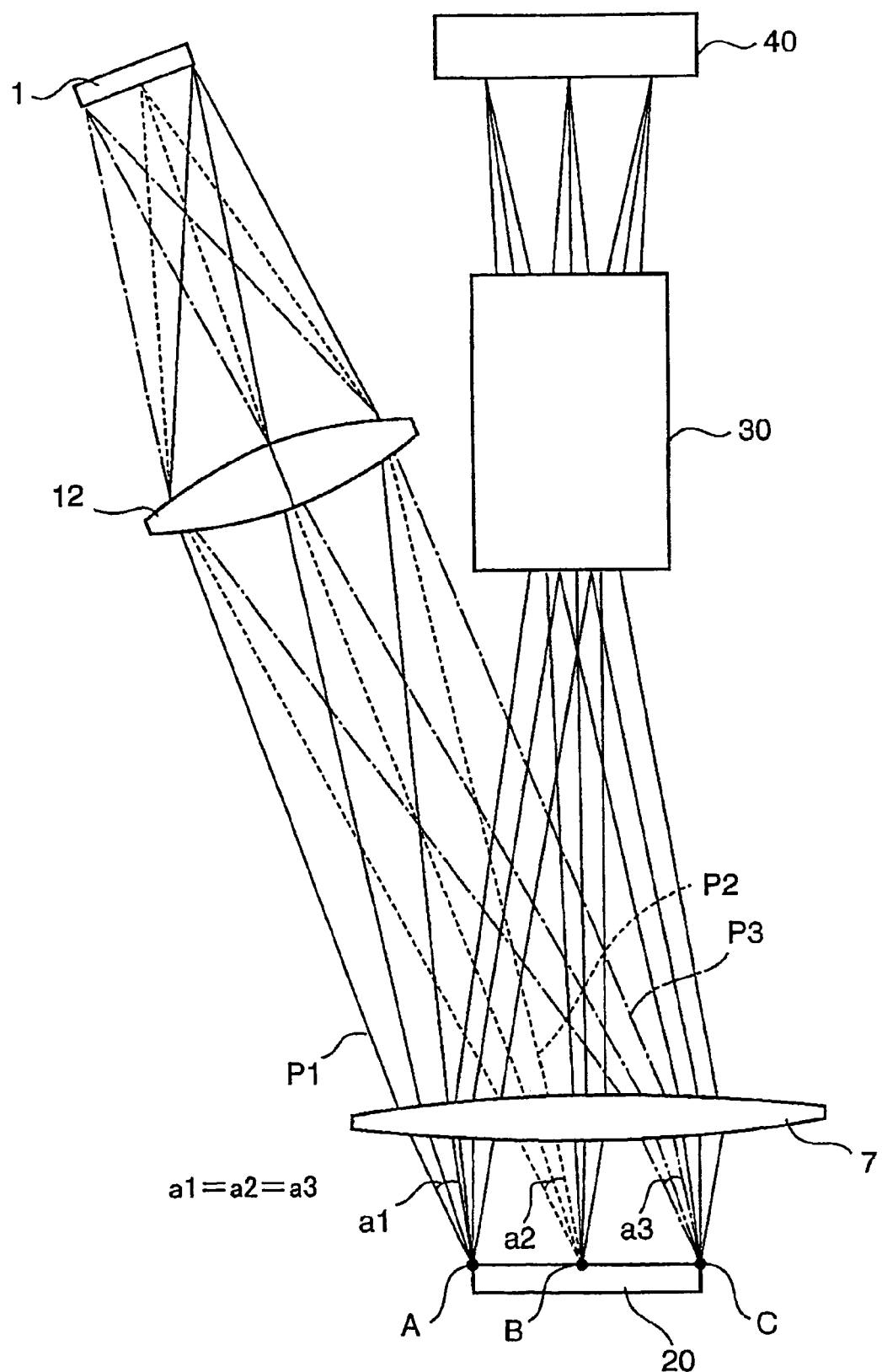
FIG. 6 is a schematic diagram showing the configuration of a reflected light measuring apparatus which employs the telecentric optical system.

To utilize this property of the telecentric optical system, a lens 7, that is, the telecentric optical system is interposed between the condenser lens 12 and the specimen 20 to be measured, as shown in FIG. 6. The apparatus is then constructed so that the measuring light is projected onto the specimen 20 through the lens 7 and the reflected light is passed again through the lens 7 and enters the light receiving sensor 40.

With the above configuration, since the measuring light rays P1, P2, and P3 to be projected onto the respective points A, B, and C on the specimen 20 are made parallel by passing through the lens 7 and thus undergoing a telecentric effect, the angular widths a1, a2, and a3 of the measuring light rays P1, P2, and P3 become the same. In this way, the projection angles of the measuring light rays to be projected onto the measuring area surface of the specimen 20 can be made the same.

Likewise, the reflected light rays produced by reflection of the measuring light rays P1, P2, and P3 are passed through the lens 7, i.e., the telecentric optical system, and enter the light receiving sensor 40, so that the reflected light rays reflected from the respective points A, B, and C and having equal angular widths are incident on the light receiving sensor 40 at the portions thereof corresponding to the points A, B, and C. As a result, the reflected light rays, reflected at the same angle from the measuring area surface of the specimen 20, can be measured by the light receiving sensor 40, and thus the measurement errors are greatly suppressed.

Next, each embodiment of the present invention will be described in detail.

Embodiment 1

Figure 7:
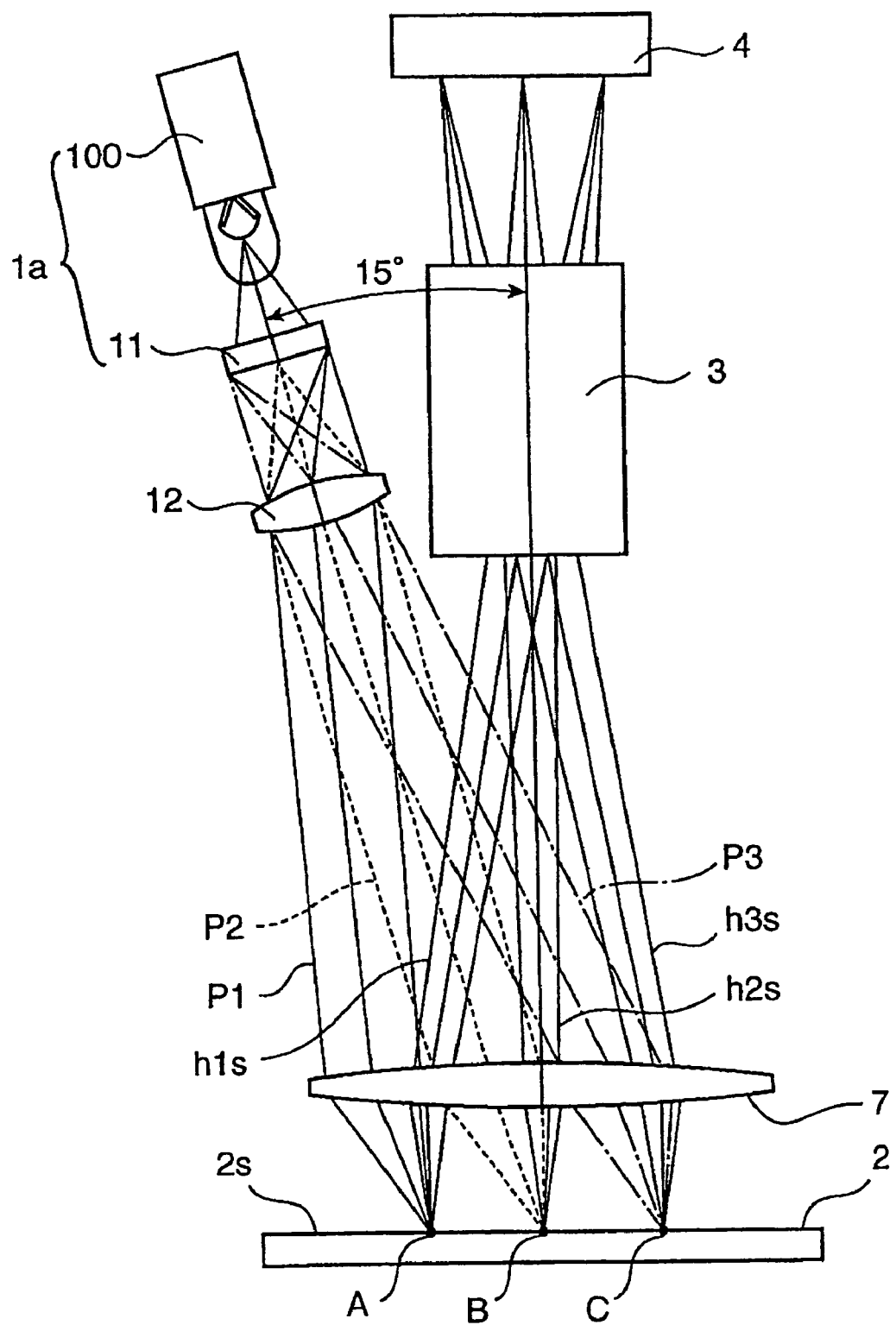
FIG. 7 is a schematic diagram showing the configuration of a reflected light measuring apparatus according to a first embodiment.

A first embodiment will be described with reference to the schematic diagram of FIG. 7.

In the configuration shown, the illumination system is an optical system comprising a light source unit 1a, a condenser lens 12, and a lens 7, and is constructed to project the measuring light onto the specimen 2 from an angle of 15° relative to the normal to the specimen 2 (measurement surface 2S). The light receiving system is an optical system comprising the lens 7, a light receiving lens 3, and a light receiving sensor 4, and is constructed to receive the reflected light rays reflected in a direction whose angle to the normal to the measurement surface 2S is 0°, out of the reflected light rays occurring as a result of the projection of the measuring light.

The lens 7 is provided to make the projection angle of the measuring light to the measuring area and the receiving angle of the reflected light from the measuring area respectively the same within the measuring area surface, and a telecentric optical system is constructed by placing the lens 7 in the light paths of the illumination system and the light receiving system (the same lens 7 is shared between the illumination system and the light receiving system).

The light source unit 1a comprises a light source 100 (a spot light source may be used) and a light diffusing member 11 for diffusing the light emitted from the light source 100. A halogen lamp, a xenon lamp, an LED lamp, or the like can be used as the light source 100. The light emitted from the light source 100 enters the light diffusing member 11 where the entering light is diffused in all directions and thus converted into light spreading uniformly over a wide range of angles; use can be made, for example, of a diffusing member, such as a frosted glass, on the surface of which microscopic irregularities are formed that scatter incident light and thus cause diffuse reflection, or of an optical component such as a diffractive optical element (DOE) that can form a diffraction pattern.

Here, it is preferable to use an optical component, such as a diffractive optical element, that can generate diffused light having angle dependence rather than randomly diffused light, because such a component can reduce light loss when the light emitted from the light source 100 passes through the light diffusing member 11. The light source unit 1a incorporating such a light diffusing member 11 provides an area light source that can project measuring light with a prescribed angular width onto each point on the measuring area surface of the specimen 2.

The condenser lens 12 has the function of collecting the light emitted from the light source unit 1a, i.e., the light passed through the light diffusing member 11, and directing it to the lens 7. More specifically, the condenser lens 12 is placed at the focal point of the light diffusing member 11, collects the light emitted from the various points on the emergence surface of the light diffusing member 11, and directs the measuring light rays, each having a prescribed angular width, to the lens 7 as shown by P1, P2, and P3 in the figure.

The lens 7 is provided so that the measuring light rays P1, P2, and P3 collected by the condenser lens 12 can be projected as parallel light rays at a given angle onto the measurement surface 2s of the specimen 20. That is, the group of measuring light rays P1, P2, and P3, which are not telecentric when emerging from the condenser lens 12, is converted into telecentric light for projection onto the measurement surface 2s. With the interposition of this lens 7, telecentric light can be projected onto the measurement surface 2s.

In the configuration shown in the present embodiment, the condenser lens 12 is interposed between the light diffusing member 11 and the lens 7; however, to simplify the optical system, the condenser lens 12 may be omitted, and the light emergence surface of the light diffusing member 11 may be placed at the focal point of the lens 7 so that the image of the light emergence surface will be focused on the measurement surface 2s of the specimen 2.

The specimen 2 to be measured is not limited to any specific type, but a specimen whose measurement surface 2s is curved, especially a specimen having a curved surface coated with metallic paint or pearly color paint (typically, a car body or the like), is preferred because the effect of the embodiment becomes greater for such a specimen.

Figure 16:
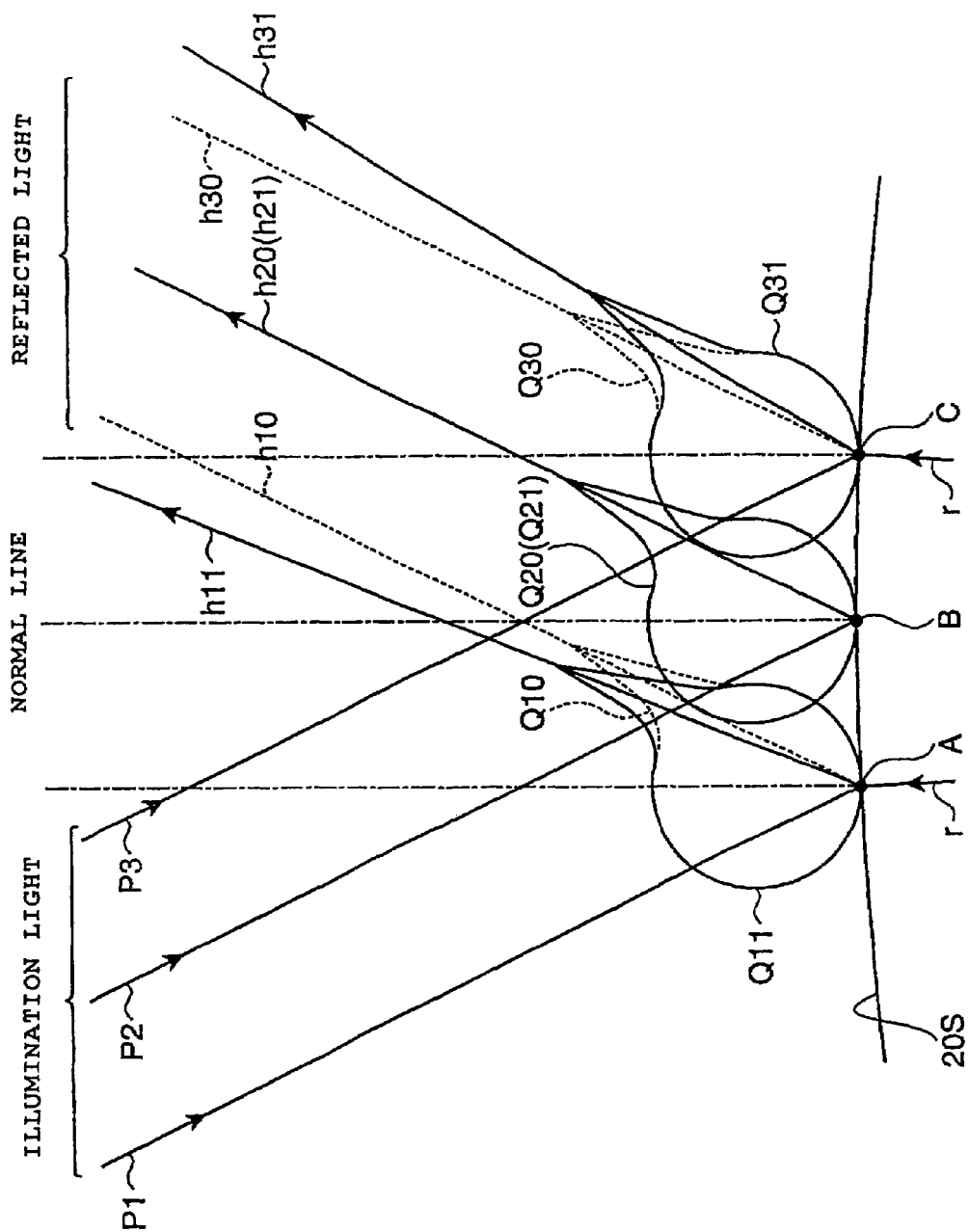
FIG. 16 is a characteristic diagram showing reflection characteristics when the measuring surface of the specimen under measurement is a curved surface.

More specifically, in metallic painting or pearly color painting, reflective materials such as thin aluminum or mica flakes are contained in the paint, and since the reflective materials are oriented in random directions in the paint, the reflected light intensity on the painted surface greatly varies depending on the viewing direction. That is, when the painted surface is illuminated with light, the light intensity greatly changes near the specularly reflected light (as shown in FIG. 2 and other reflection characteristic diagrams, the portion near the specularly reflected light is sharply pointed compared with other portions); this shows that a curved specimen is susceptible to variations in reflection characteristic as previously described with reference to FIGS. 16 and 17. It can therefore be said that curved specimens coated with metallic paint or pearly color paint are particularly suitable for the purpose contemplated by the present embodiment.

The lens 7 also serves the function of providing a telecentric optical system for the receiving system. That is, of the reflected light rays produced by reflecting the measuring light rays P1, P2, and P3 off the measurement surface 2s, the light rays having the prescribed angular width and reflected at equal angles are directed as measuring reflected light rays h1s, h2s, and h3s to the light receiving lens 3. More specifically, of the light rays reflected (emitted) from the measuring area on the measurement surface 2s, only the parallel light rays having the prescribed angular width are directed to the receiving lens by the telecentric effect of the lens 7.

The receiving light lens 3 has the function of directing the measuring reflected light rays h1s, h2s, and h3s, produced by reflection from the measuring area on the measurement surface 2s, to the receiving light sensor 4. Various kinds of optical member or system can be used for the light receiving lens 3; for example, use can be made of a condenser lens, a camera lens, an optical system having a finite focus, or an optical system that diffuses received light.

The light receiving sensor 4 serves as a sensing element for converting the measuring reflected light rays h1s, h2s, and h3s, directed from the light receiving lens 3, into electrical signals, and for detecting reflection characteristics by analyzing the light intensities or wavelengths, phases, etc. The light receiving sensor 4 is placed at the focal point of the light receiving lens 3. For the light receiving sensor 4, use can be made of a spot-like photo sensor such as a photodiode, or a two-dimensional photo sensor such as a CCD.

The lens 7 is not limited to any specific type, the only requirement being that the lens be of a type that can achieve a telecentric optical system; for example, as earlier described with reference to FIG. 5, a convex lens or the like can be used that achieves an image-side telecentric optical system having the property that the principal rays on the image side do not intersect the optical axis however far they are extended.

Next, a description will be given of a reflected light measuring method that uses the apparatus constructed as described above. First, the light source 100 in the light source unit 1a is turned on by a light producing circuit not shown, and the light emitted from the light source 100 is incident on the light diffusing member 11. The incident light is scattered by the light diffusing member 11 and emerges as scattered light (or as diffracted light when a diffractive optical element is used as the light diffusing member 11) from the emergence surface of the light diffusing member 11.

In this way, the light (measuring light) emitted from the light source unit 1a emerges as uniformly distributed surface area light, not as nonuniformly distributed surface area light, from the entire emergence surface of the light diffusing member 11. Accordingly, the measuring light can be projected as the measuring light rays P1, P2, and P3 each having a prescribed angular width onto the respective points on the measuring area surface of the specimen 20.

The measuring light rays P1, P2, and P3 emitted from the light source unit 1a enters the condenser lens 12, and are directed through the condenser lens 12 toward the lens 7. At this time, since the illumination system is tilted only 15° relative to the normal to the measurement surface 2s, as previously described, that is, since the projection angle of the measuring light relative to the normal to the specimen surface is relatively small, the parallelism of the measuring light rays P1, P2, and P3 is not assured here.

Then, the measuring light rays P1, P2, and P3 entering the lens 7 are converted into parallel light rays by undergoing the telecentric effect as they pass through the lens 7, and the measuring light rays P1, P2, and P3 thus made parallel to each other are projected onto the respective points A, B, and C on the measurement surface 2s of the specimen 2. In this way, the measuring light rays can be projected at the same angle to the measuring area surface whose reflections are to be measured.

Next, the reflected light rays from the respective points A, B, and C on the measurement surface 2s again pass through the lens 7. Here, the lens 7, the light receiving lens 3, and the light receiving sensor are together constructed as a telecentric optical system; therefore, of the reflected light rays from the respective points A, B, and C, only the light rays that are parallel to each other between the measurement surface 2s and the lens 7 and are reflected in the direction coinciding with the direction of the normal to the measurement surface 2s (the mounting angle of the receiving system is, as previously described, 0° relative to the normal and thus coincides with the direction of the normal) are directed as the measuring reflected light rays h1s, h2s, and h3s from the lens 7 to the light receiving lens 3. Finally, the measuring reflected light rays h1s, h2s, and h3s are focused on the light receiving surface of the light receiving sensor 4 through the light receiving lens 3, and the desired sensing is thus accomplished.

As described above, since the measuring light rays P1, P2, and P3, each having a prescribed angular width, are projected (via the telecentric optical system) at the same angle to the respective points on the measuring area surface of the specimen 2, and since the reflected light is received via the telecentric optical system, the reflected light can be measured by suppressing error causing factors as far as possible, even when the specimen 2 to be measured is a curved specimen (that is, the measurement surface 2s is a curved surface).

Embodiment 2

A second embodiment will be described with reference to FIG. 8.

Figure 8:
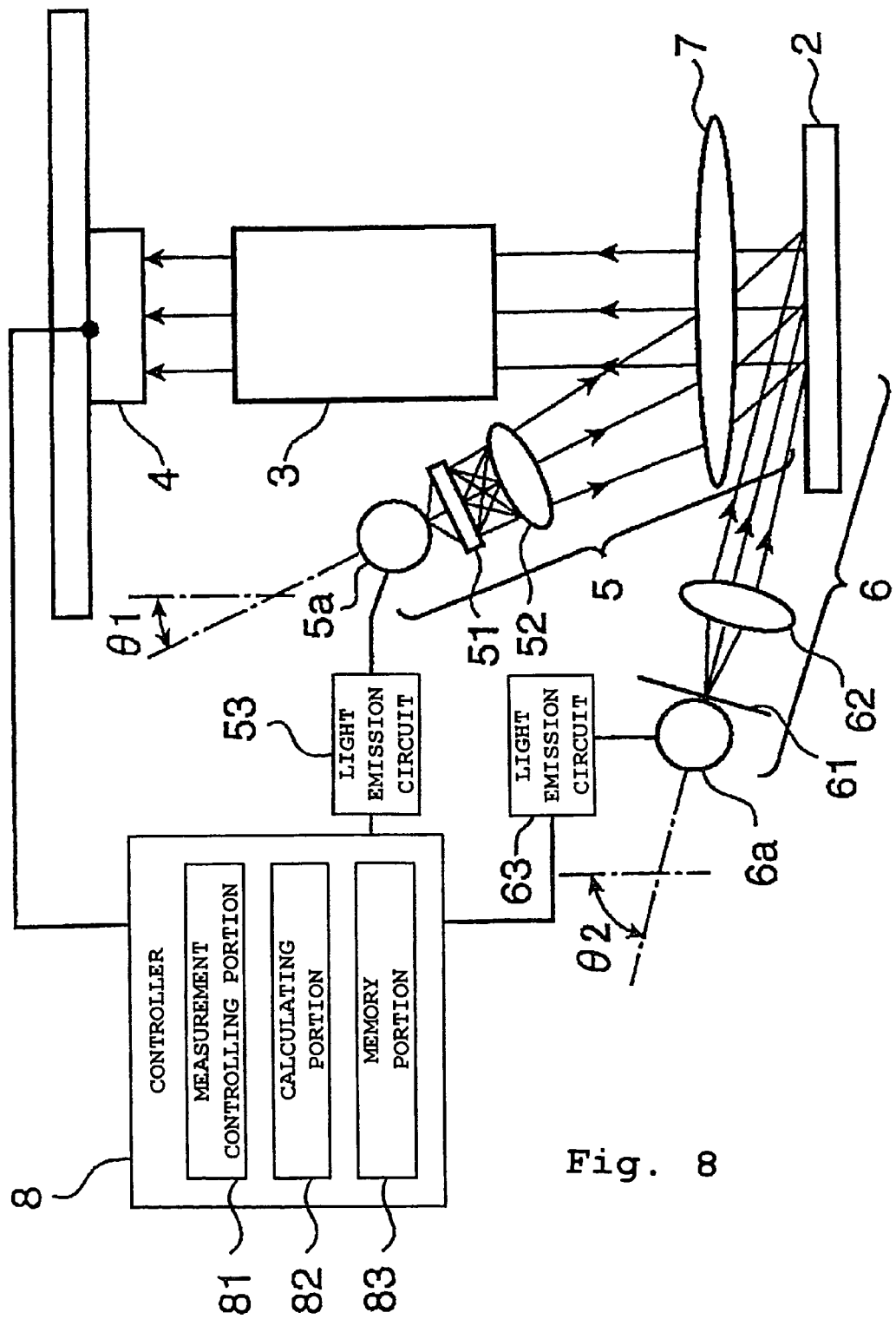
FIG. 8 is a schematic diagram showing the configuration of a reflected light measuring apparatus according to a second embodiment.

FIG. 8 is a schematic diagram showing one example of a reflected light measuring apparatus employing a multidirectional illumination, unidirectional light receiving method which is used, for example, in a multi-angle calorimeter or the like. The basic configuration of this reflected light measuring apparatus is the same as that of the first embodiment, the only difference being that the measuring light is projected onto the specimen 2 from a plurality of angles.

The example shown in FIG. 8 uses two light illumination systems: a highlight illumination system 5 whose angle of measuring light projection (indicated by θ1 in the figure) relative to the normal to the surface of the specimen 2 is relatively small (for example, θ1=15 degrees), and a shade illumination system 6 whose angle of measuring light projection (indicated by θ2 in the figure) relative to the normal to the specimen surface is relatively large (for example, θ2=75 degrees) The highlight illumination system 5 comprises a light source 5a, a light diffusing member 51, and a lens 52. On the other hand, the shade illumination system 6 comprises a light source 6a, a beam regulating plate 61, and a condenser lens 62. Here, spot light sources may be used as the light sources 5a and 6a.

The light emitting operation of the light sources 5a and 6a is controlled by light producing circuits 53 and 63, respectively, and the operation of the light producing circuits 53 and 63 is controlled by a control unit 8. The control unit 8 comprises a CPU, etc. and includes a measurement controller 81, a processor 82, and a memory 83. The measurement controller 81 controls the light emitting operation of the light sources 5a and 6a for reflected light measurement, and generates light emission control signals and transmits them to the light producing circuits 53 and 63.

The processor 82 computes the necessary reflection characteristic values based on received-light data (reflected light amount data, etc.) supplied from the light receiving sensor 4 that received the reflected light from the specimen 2 under measurement. The memory is constructed from a RAM or an EEPROM or the like, and stores the measured values of the reflection characteristics, a measuring program, etc.

In the above configuration, the highlight illumination system 5 is similar in configuration to the illumination system of the first embodiment which comprises the light source unit 1a. That is, the light diffusing member 51 is placed in front of the light source 5a, and the lens 7 is interposed between the condenser lens 52 and the specimen 2, thus achieving a telecentric optical system similar to that of the first embodiment. With this configuration, highly parallel light rays having a prescribed angular width can be projected onto the specimen to be measured.

On the other hand, the shade illumination system 6 is constructed to project the measuring light onto the specimen 2 without employing a telecentric optical system (this illumination system is similar to that shown in FIG. 1A). More specifically, the light emitted from the light source 6a is introduced directly into the optical lens 62 without the intervention of a light diffusing member or the like, and the light emerging from the lens 62 is projected onto the specimen 2 by passing through the space between the specimen 2 and the lens 7 which is a constituent element of the telecentric optical system. This is because, since the measuring light projection angle θ2 (the angle relative to the normal to the specimen surface) of the shade illumination system 6 is relatively large, the parallelism of the measuring light can be easily ensured without constructing a telecentric optical system, as earlier described, and no appreciable errors occur even when the specimen 20 is a curved specimen.

Further, since the measuring light projected from the shade illumination system 6 is incident obliquely on the specimen 2, the reflection angle of its specular reflection is approximately equal to the projection angle θ2 of the measuring light. Accordingly, in the present embodiment which is constructed to receive reflected light reflected in a direction parallel to the normal to the specimen 2, the reflection characteristic portion associated with the diffuse reflection having no angle dependence, not the reflection characteristic portion that has a sharp point near the specular reflection, is received as the reflected light of the measuring light projected from the shade illumination system 6. For this reason also, there is little need to construct the shade illumination system 6 as a telecentric optical system.

Next, a description will be given of a reflected light measuring method that uses the above-described apparatus. First, to start the measuring light projection from the highlight illumination system 5, the light producing circuit 53 is operated by the control signal from the measurement controller 81 in the control unit 8, and the measuring light is emitted as needed from the light source 5a. Thereafter, as in the first embodiment, the light is converted by the light diffusing member 51 into surface area light which is then collected by the condenser lens 52 and directed to the lens 7. The light is then converted by the lens 7 into parallel light which is projected onto the specimen 2.

Likewise, to start the measuring light projection from the shade illumination system 6, the light producing circuit 63 is operated by the control unit, and the measuring light is emitted as needed from the light source 6a. Then, the measuring light passes through the beam regulating plate 61 and the optical lens 62 placed at the focal point, and is projected onto the specimen 2 through the space between the lens 7 and the specimen 2 (i.e., from a direction tilted θ2 relative to the normal to the specimen) without passing through the lens 7 that forms part of the telecentric optical system.

The reflected light of the measuring light projected from each of the highlight illumination system 5 and the shade illumination system 6 is passed through the lens 7 of the telecentric optical system, and received by the light receiving sensor 4 through the light receiving lens 3. Of the reflected light of the measuring light projected from the highlight illumination system 5, only the reflected light rays parallel to each other between the specimen 2 and the lens 7 are directed to the light receiving sensor 4 by the effect of the telecentric optical system similar to that described in the first embodiment. On the other hand, the reflected light of the measuring light projected from the shade illumination system 6 does not specifically need correction by the telecentric optical system, but this reflected light is also passed through the lens 7 and directed to the light receiving sensor 4, because the lens 7 is placed in the receiving light path.

The received-light data detected by the light receiving sensor 4 is supplied to the processor 82 in the control unit 8, and the measured values of the reflection characteristics are output, for example, as multi-angle measured color values. The present embodiment has shown an example in which the measuring light is projected from two different angles, but the apparatus may be configured so that the measuring light is projected from three or more angles.

In that case, it is desirable that any illumination system whose angle of measuring light projection (indicated by θ1 in the figure) relative to the normal to the surface of the specimen 2 is relatively small (for example, smaller than about 40°) be constructed as a telecentric optical system like the highlight illumination system 5. Further, in the highlight illumination system 5, the condenser lens 52 may be omitted, and the light diffusing member 51 may be placed at the focal point of the lens 7.

Embodiment 3

Figure 9:
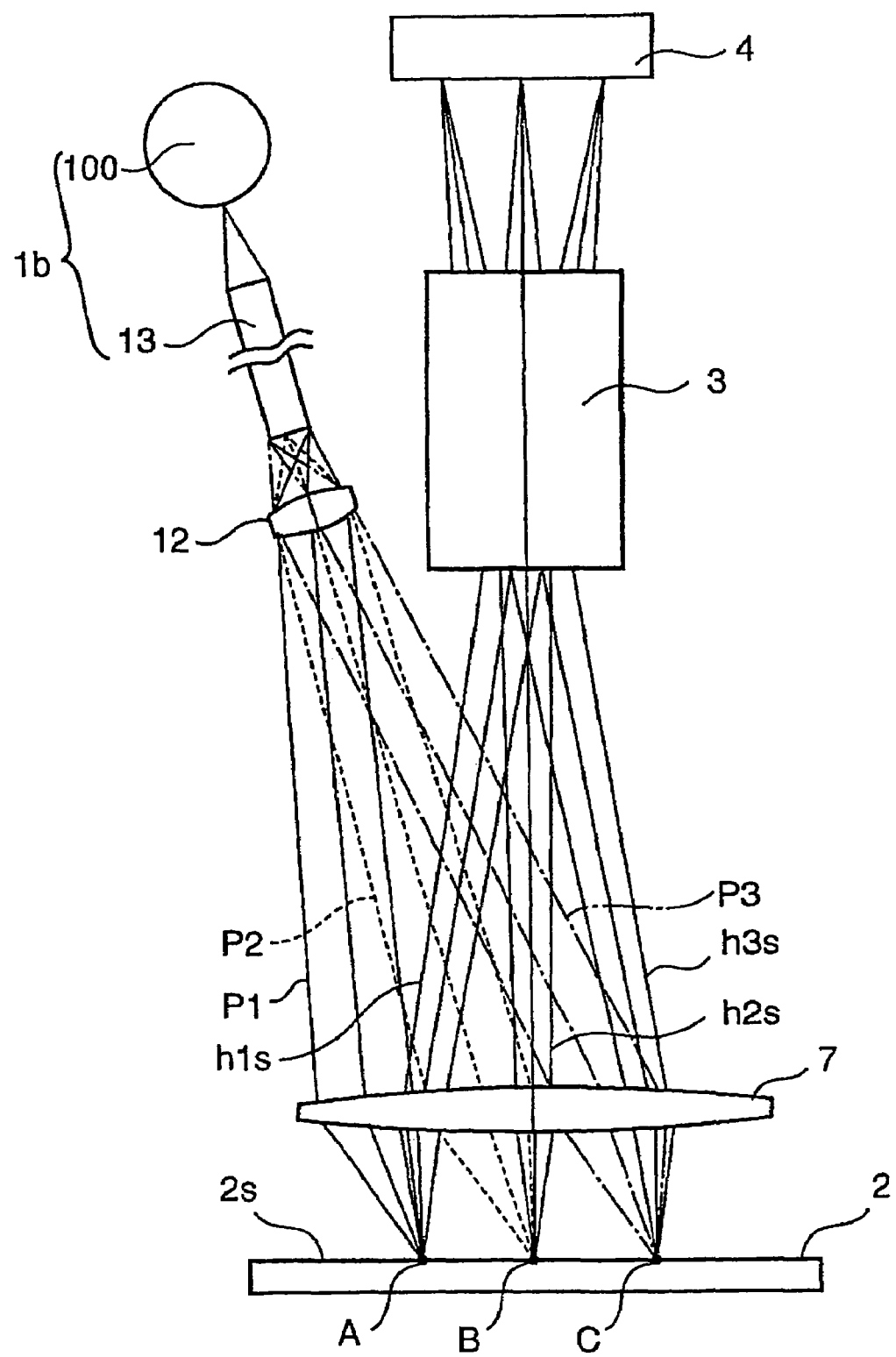
FIG. 9 is a schematic diagram showing the configuration of a reflected light measuring apparatus according to a third embodiment.
Figure 10:
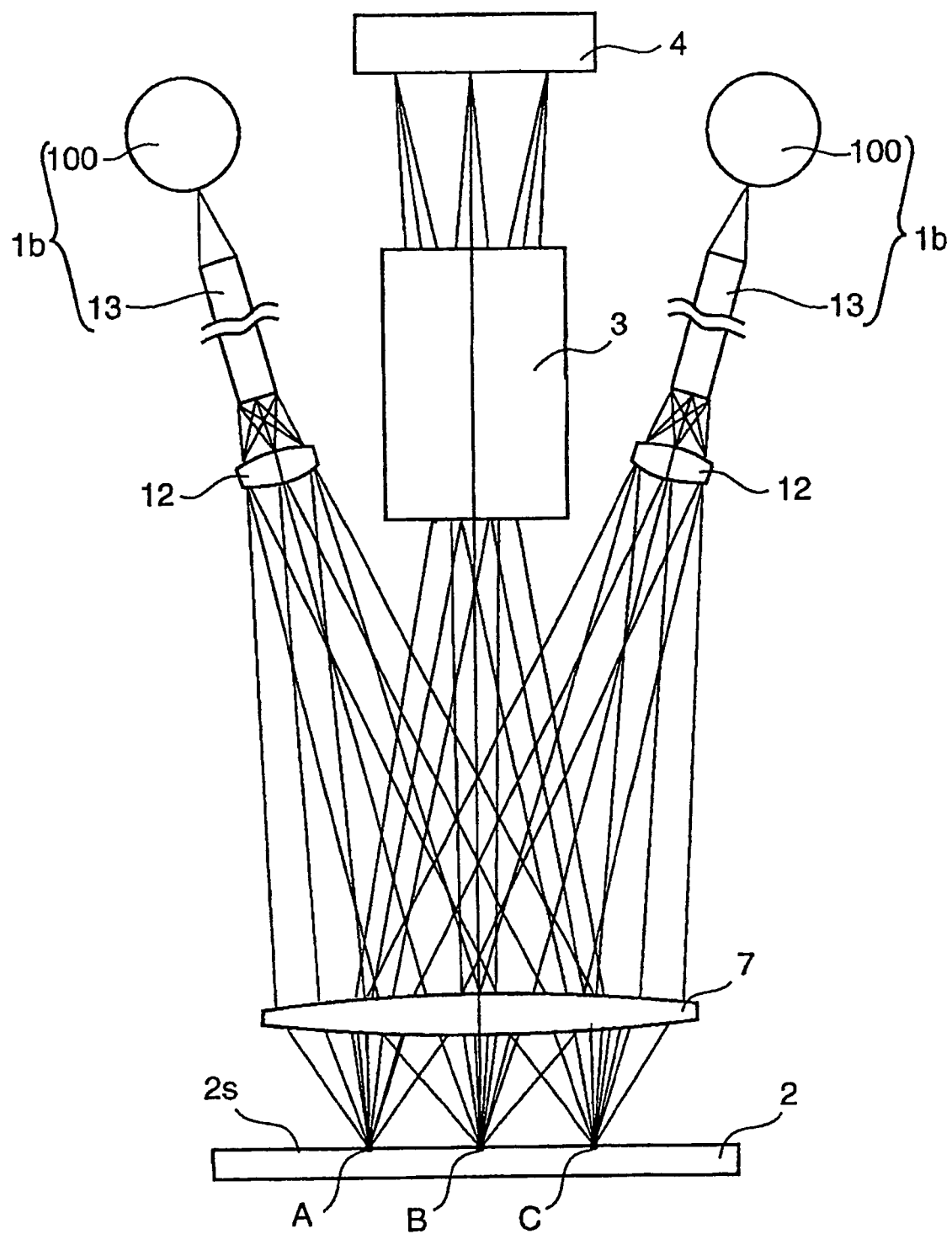
FIG. 10 is a schematic diagram showing a modified example of the reflected light measuring apparatus of the third embodiment.
Figure 11:
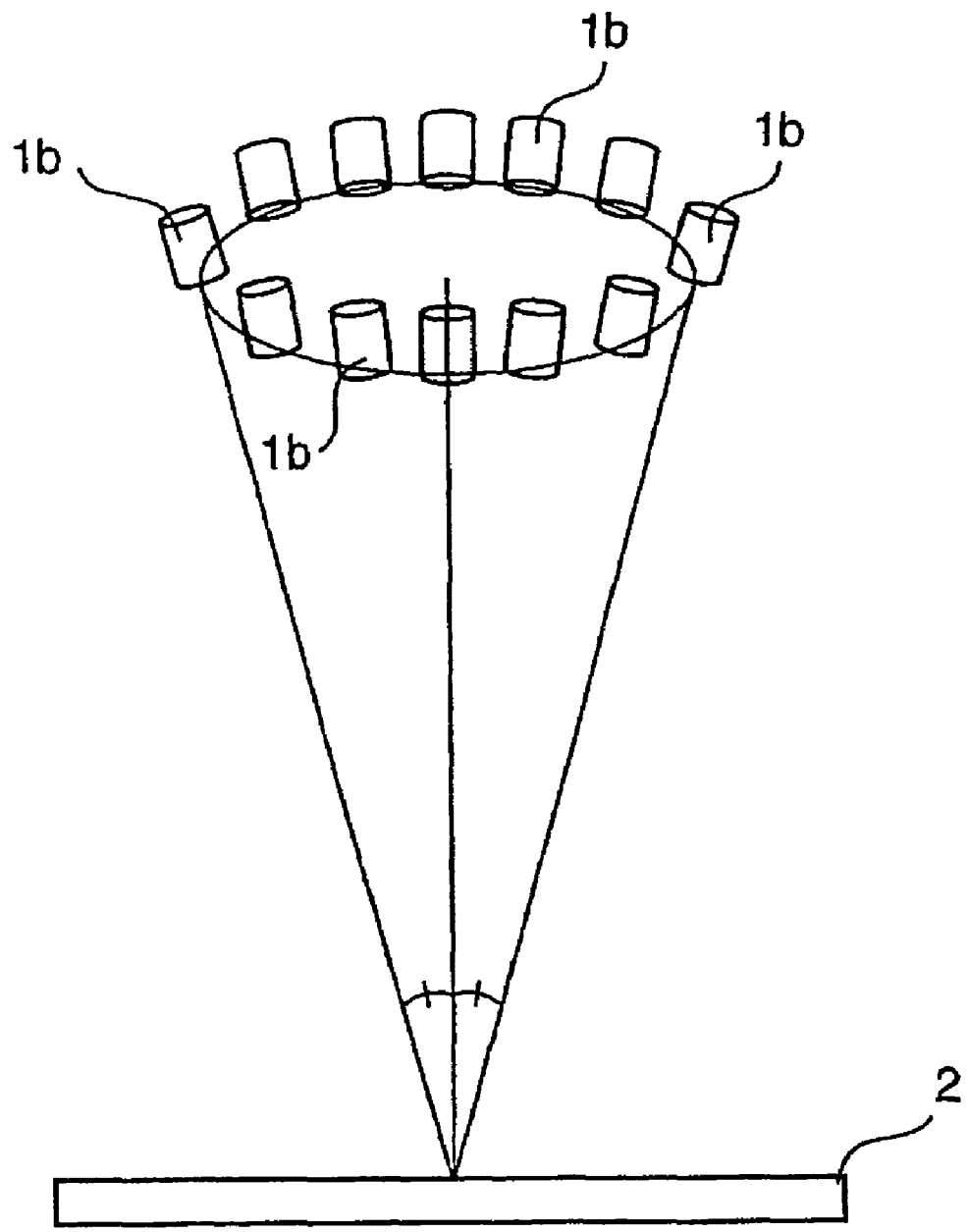
FIG. 11 is a schematic diagram showing another modified example of the reflected light measuring apparatus of the third embodiment.

The third embodiment shown in FIGS. 9 to 11 concerns a reflected light measuring apparatus in which the light source unit 1a in the first embodiment is replaced by a different type of light source unit 1b. This embodiment is the same as the first embodiment except for the light source unit 1b, and the description of the same elements as those in the first embodiment will not be repeated here.

The light source unit 1b of this embodiment comprises a light source 100 and an optical fiber 13 into which the light emitted from the light source 100 is introduced. For the optical fiber 13, use can be made of a silica glass-based optical fiber or a plastic-based optical fiber, and it is desirable to use a fiber having a suitable heat resistant cladding layer, buffer layer, etc.

The optical fiber 13 may be constructed from a single fiber or from a plurality of fibers grouped together. When using a single fiber, it is preferable to use a fiber having a large diameter and a high numerical aperture (NA), because the light emitting surface area can be made large. On the other hand, when constructing the optical fiber by grouping together a plurality of fibers, the plurality of fibers may be arranged side by side and covered with a coating layer to form a tape-like optical fiber, or may be bundled together to form a fiber bundle whose cross section is circular. In particular, the fiber bundle is preferred because the light from the light source 100 can be effectively converted into surface area light, and because the light can be easily projected onto the condenser lens 12 and the optical system can be easily formed.

According to the light source unit 1b provided with the optical fiber 13 described above, the light emitted from the light source 100 is incident on one end face of the optical fiber 13 having a prescribed aperture area size (cross sectional area of the core) and propagates through the optical fiber 13 until it reaches the opposite end face from which the light emerges.

At this time, the light emerges as surface area light that matches the cross sectional area of the core at the end face of the optical fiber 13. This means that the spot-like light source is converted into an area light source, so that the light is projected as surface area light onto the condenser lens 12 located forward. The light passed through the condenser lens 12 emerges as measuring light rays P1, P2, and P3 which are directed to the lens 7 of the telecentric optical system; the operation thereafter is the same as that described in the first embodiment.

The reflected light measuring apparatus shown in FIG. 10 is a modified example of the third embodiment, in which a plurality of light source units 1b, each comprising a light source 100 and an optical fiber 13 into which the light emitted from the light source 100 is introduced, are provided to illuminate the same specimen 2.

The two light source units 1b and 1b are symmetrically arranged with one tilted in the opposite direction to the other so as to provide the same projection angle relative to the normal to the specimen 2, so that the measuring light emitted from each of the two light source units 1b and 1b is directed to the same lens 7 through the corresponding condenser lens 12. Since the plurality of light source units 1b and 1b are arranged in the same plane so as to provide the same projection angle, this offers the advantage of being able to achieving illumination (projection of the measuring light) that can suppress the unevenness in illumination brightness on the measuring area surface of the specimen 2 as much as possible.

FIG. 11 shows another modified example of the third embodiment, in which many light source units 1b, each comprising a light source 100 and an optical fiber 13 into which the light emitted from the light source 100 is introduced, are arranged in a ring around a center axis normal to the specimen 2. In this example also, the many light source units 1b, 1b, . . . are arranged with each unit tilted so as to provide the same projection angle relative to the normal to the specimen 2, so that the Measuring light emitted from any one of the light source units 1b, 1b, . . . is directed to the same lens (not shown in FIG. 11) through the corresponding condenser lens. By arranging the many light source units 1b, 1b, . . . in a ring as described above, the measuring light can be projected in a manner that further suppresses the unevenness in illumination brightness on the measuring area surface of the specimen 2.

When applying the above third embodiment to a multi-angle calorimeter or the like, the light source unit 1b should be configured as the highlight illumination system and, in addition to that, a shade illumination system should be provided so as to be able to project measuring light by passing through the space between the lens 7 and the specimen to be measured. In this case, it is desirable to provide a plurality of shade illumination systems arranged so as to project the measuring light at the same angle.

In the examples shown in FIGS. 10 and 11, each light source unit 1b may of course be equipped with its own light source 100, but from the standpoint of simplifying the apparatus construction and reducing the power consumption, it is desirable to use only one light source 100 and to configure the apparatus so that the light emitted from the light source 100 is introduced into a plurality of optical fibers 13. In a specific example that implements such configuration, the end face side of the optical fiber 13 that faces the light source 100 is constructed from a bundle of fibers, and the bundle is separated into groups of one or a plurality of fibers toward the opposite end face side that faces the respective condenser lenses.

Embodiment 4

Figure 12:
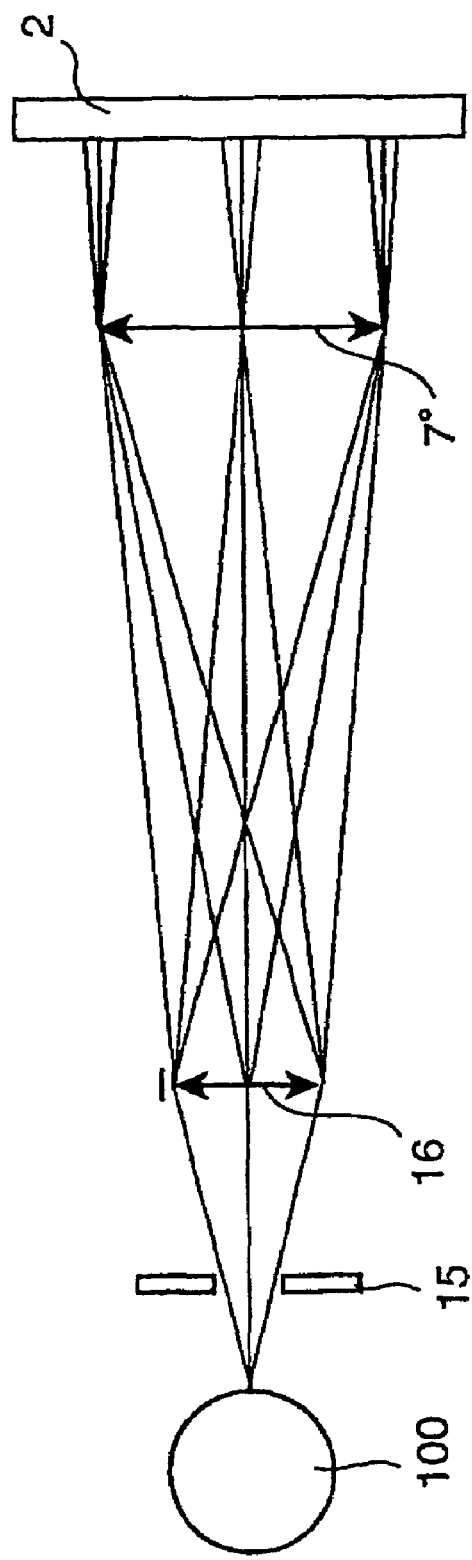
FIG. 12 is a schematic diagram showing an essential portion of the configuration of a reflected light measuring apparatus according to a fourth embodiment.
Figure 13:
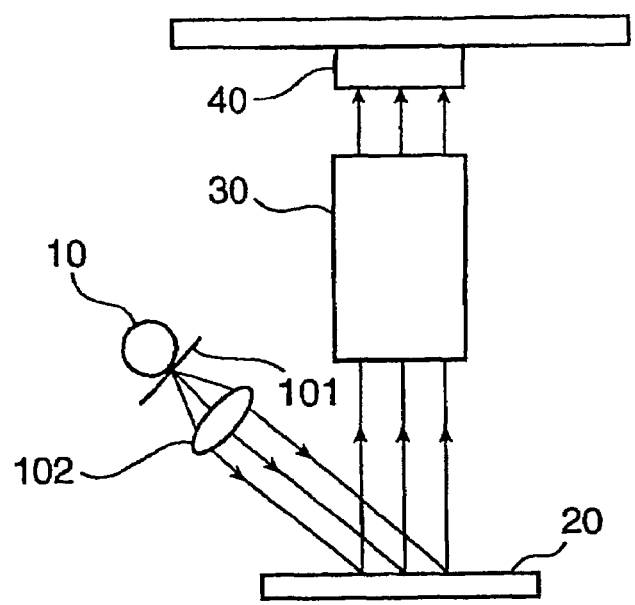
FIG. 13 is a schematic diagram showing the basic configuration of a reflected light measuring apparatus according to the prior art.
Figure 14:
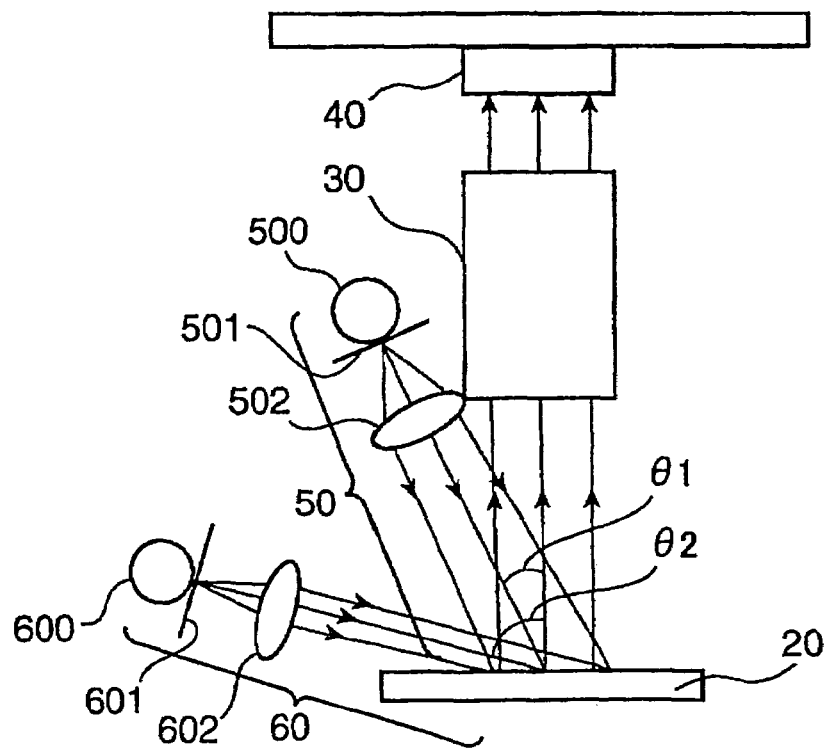
FIG. 14 is a schematic diagram showing the configuration of a reflected light measuring apparatus employing a multidirectional illumination, unidirectional light receiving method according to the prior art.

FIG. 12 is a schematic diagram showing an embodiment in which the light source unit 1a (illumination system) in the first embodiment is modified to achieve Koehler illumination. In this embodiment also, the configuration other than the Koehler illumination system is the same as that of the first embodiment; in FIG. 12, the light receiving system is not shown.

The illumination system of this embodiment comprises a light source 100, a condenser lens 16, an aperture stop mechanism 15 interposed therebetween as needed, and a lens 7 for constructing a telecentric optical system. In this configuration also, the light emitted from the light source 100 is passed through the condenser lens 16 and is converted by the lens 7 into parallel rays of light for projection onto the specimen 2 under measurement, but the lenses are arranged so that the light source image will not be focused directly on the specimen 2.

That is, the condenser lens 16 is placed at a position spaced away from the lens 7 by a distance equal to the focal length of the lens 7, and the lens 7 is placed at the focus point of the light source 100 (that is, the lenses are arranged to achieve Koehler illumination). The aperture stop mechanism 15 has the function of controlling the field of view and limiting the illumination range by shutting off unwanted illumination light; by placing the aperture stop mechanism 15 before the condenser lens 16, the incidence angle of the measuring light can be provided with redundancy.

According to the thus configured illumination system, the emergence surface of the condenser lens 16 acts as if it were an area light source, and the measuring light can be projected with a prescribed angular width onto each point on the measuring area surface of the specimen 2. According to this configuration, without using the light diffusing member 11 or the like used in the first embodiment, the same effect can be obtained by just adjusting the positional relationship between the condenser lens 16 and the lens 7, offering the advantage of being able to simplify the optics of the illumination system.

The various embodiments has been described, but it should be understood that the present invention is not limited to the specific embodiments described herein. For example, the light source 100 has been combined with the light diffusing member 11 or the optical fiber 13 to construct an area light source, but alternatively, the area light source may be constructed by combining a plurality of spot-like light sources. For example, a plurality of light emitting devices such as LEDs may be arranged in an array or in a grid pattern on a substrate to construct the area light source. Such configuration has the advantage that the area light source can be constructed in a simple structure, serving to simplify the optics of the illumination system.

The reflected light measuring apparatus described above comprises an illumination system which projects measuring light onto a measuring area of an object to be measured, and a light receiving system which receives reflected light from the measuring area illuminated with the measuring light projected from the illumination system, wherein the illumination system is configured to be able to project the measuring light with a prescribed angular width onto each point in the measuring area of the object to be measured, and the illumination system and the light receiving system are configured to project the measuring light onto the measuring area and receive the reflected light from the measuring area, respectively, via a telecentric optical system.

Further, in the reflected light measuring apparatus, a lens for making the projection angle of the measuring light to the measuring area and the receiving angle of the reflected light from the measuring area respectively the same within the measuring area is placed in the light paths of the illumination system and the light receiving system to construct the telecentric optical system.

In the above configuration, the illumination system may be constructed by incorporating a light source unit comprising a light source and a light diffusing member for scattering the light emitted from the light source.

Alternatively, the illumination system may be constructed by incorporating a light source unit comprising a light source and an optical fiber into which the light emitted from the light source is introduced. In this case, it is preferable to construct the optical fiber from a bundle of fibers. Further, the illumination system may be constructed by incorporating a Koehler illumination system. Alternatively, the illumination system may be constructed by incorporating a light source unit having a plurality of spot light sources.

The reflected light measuring apparatus described above comprises an illumination system which projects measuring light onto a measuring area of an object to be measured, and a light receiving system which receives reflected light from the measuring area illuminated with the measuring light projected from the illumination system, wherein the illumination system includes a highlight illumination system which projects the measuring light from a direction whose angle to a normal to the measuring area of the object to be measured is relatively small and a shade illumination system which projects the measuring light from a direction whose angle to the normal to the measuring area of the object to be measured is relatively large, and wherein the highlight illumination system is configured to be able to project the measuring light with a prescribed angular width onto each point in the measuring area of the object to be measured, and the highlight illumination system and the light receiving system are configured to project the measuring light onto the measuring area and receive the reflected light from the measuring area, respectively, via a telecentric optical system.

In the above configuration of the reflected light measuring apparatus employing a multidirectional illumination, unidirectional light receiving method, provisions are made to suppress an error at least for the highlight illumination system which projects the measuring light from the direction whose angle to the normal to the measuring area of the object to be measured is relatively small.

The reflected light measuring method described above projects measuring light onto a specimen having a curved surface and measures a reflection characteristic by receiving the resulting reflected light, wherein the measuring light is projected with a prescribed angular width onto each point on the curved surface of the specimen, and the measurement is performed by making the projection angle of the measuring light to the curved specimen and the receiving angle of the reflected light from the curved specimen respectively the same within the curved surface of the specimen through the use of a telecentric optical system. Here, the method is particularly advantageous when the curved specimen is coated with metallic paint or pearly color paint.

According to the thus configured reflected light measuring apparatus, since the measuring light from the illumination system is projected with a prescribed angular width onto each point in the measuring area of the object to be measured, the resulting reflection characteristic is such that the sharpness of the characteristic near its specular reflection is reduced, thus suppressing an error associated with an angular change; as a result, even when the measuring surface area is a curved surface, the reflected light can be measured without incurring an appreciable error. Further, since the measuring light is projected onto the measuring area via the telecentric optical system and the reflected light is received from the measuring area again via the telecentric optical system, the projection angle of the measuring light to be projected and the receiving angle of the reflected light to be received can be made uniform; this also serves to suppress the measurement error. Therefore, even in a measuring environment in which the measuring area surface is a curved surface which inevitably causes differences in reflection characteristics, the reflected light measuring apparatus can suppresses the occurrence of errors as far as possible and without incurring an increase in apparatus size.

When the lens for making the projection angle of the measuring light and the receiving angle of the reflected light respectively the same within the measuring area is placed in the light paths of the illumination system and the light receiving system to construct the telecentric optical system, the reflected light measuring apparatus can be constructed without substantially increasing the complexity of the optical system. This offers the advantage that the apparatus size does not increase, nor does the number of parts increase appreciably.

There is also the advantage that the illumination system capable of projecting the measuring light with a prescribed angular width onto each point in the measuring area of the object to be measured can be achieved by providing a simple configuration comprising a combination of a light source and a light diffusing member and thus forming an area light source capable of producing light of uniform brightness. Further, in this case, the alignment of the optical axis between the light source and the light diffusing member can be easily accomplished, which serves to simplify the apparatus configuration.

When the illumination system is constructed by incorporating a light source unit comprising a light source and an optical fiber into which the light emitted from the light source is introduced, an area light source capable of producing light of uniform brightness can be easily formed. In particular, when the optical fiber is constructed from a fiber bundle by bundling together a plurality of optical fibers, a large surface area light source can be easily formed.

Further, when the illumination system is constructed by incorporating a Koehler illumination system, there is the advantage that the area light source can be constructed easily without specifically using the light diffusing member or the like.

When the illumination system is constructed by incorporating a light source unit having a plurality of light sources, there is the advantage that the area light source can be easily constructed.

According to the reflected light measuring apparatus employing a multidirectional illumination, unidirectional light receiving method, the highlight illumination system which projects the measuring light from the direction whose angle to the normal to the measuring area of the object to be measured is relatively small is configured to project the measuring light with a prescribed angular width onto each point in the measuring area of the object to be measured, and provisions are made to project the measuring light onto the measuring area and receive the reflected light from the measuring area via the telecentric optical system. Therefore, even in a measuring environment in which the measuring area surface is a curved surface which inevitably causes differences in reflection characteristics, the occurrence of errors can be suppressed as far as possible, and this can be accomplished without incurring an increase in apparatus size.

The reflected light measuring method described above has similar advantages to those offered by the above reflected light measuring apparatus. Among others, when the curved specimen is coated with metallic paint or pearly color paint, the above-described reflected light measuring method is particularly advantageous because such painted surfaces have the property that the reflected light intensity greatly varies depending on the viewing angle.

Although the present invention has been fully described by way of examples with reference to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A reflected light measuring apparatus comprising:
   an illumination system which projects measuring light onto a measuring area of an object to be measured; and
   a light receiving system which receives reflected light from the measuring area illuminated with the measuring light projected from the illumination system, wherein, the illumination system includes a first illumination system which projects the measuring light from a direction whose angle to a normal to the measuring area of the object to be measured is relatively small and a second illumination system which projects the measuring light from a direction whose angle to the normal to the measuring area of the object to be measured is relatively large, and wherein, the first illumination system is configured to be able to project the measuring light with a prescribed angular width onto each point in the measuring area of the object to be measured, and the first illumination system and the light receiving system are configured to project the measuring light onto the measuring area and receive the reflected light from the measuring area, respectively, via a telecentric optical system.

2. In a reflected light measuring method which projects measuring light onto a specimen having a curved surface and measures a reflection characteristic by receiving the resulting reflected light, the method further comprising projecting the measuring light with a prescribed angular width onto each point on the curved surface of the specimen, and the measurement is performed by making a projection angle of the measuring light to the specimen and a receiving angle of the reflected light from the specimen respectively the same within the curved surface of the specimen through the use of a telecentric optical system.

3. The reflected light measuring method according to claim 2, wherein, the specimen is coated with metallic paint or pearly color paint.

4. The reflected light measuring apparatus according to claim 1, wherein, the telecentric optical system includes a lens for making a projection angle of the measuring light to the measuring area and a receiving angle of the reflected light from the measuring area respectively the same within the measuring area arranged in light paths of the illumination system and the light receiving system.

5. The reflected light measuring apparatus according to claim 1, wherein, the first illumination system includes a light source unit comprising a light source and a light diffusing member for scattering light emitted from the light source.

6. The reflected light measuring apparatus according to claim 1, wherein, the second illumination system projects the measuring light onto the measuring area without employing the telecentric optical system.

* * * * *

UNITED STATES PATENT AND TRADEMARK OFFICE
CERTIFICATE OF CORRECTION

PATENT NO.         : 7,508,522 B2                                    Page 1 of 1
APPLICATION NO.    : 11/047970
DATED              : March 24, 2009
INVENTOR(S)        : Yutaka Kadowaki et al.

It is certified that error appears in the above-identified patent and that said Letters Patent is hereby corrected as shown below:

On the Title Page

Item (75), delete "Sakai" and substitute --Osaka-- in its place (all occurrences).

Signed and Sealed this

Eleventh Day of August, 2009

David J. Kappos
*Director of the United States Patent and Trademark Office*